(12) United States Patent
Larson

(10) Patent No.: US 10,265,010 B2
(45) Date of Patent: Apr. 23, 2019

(54) SENSOR-BASED SYSTEMS AND METHODS FOR MONITORING MATERNAL POSITION AND OTHER PARAMETERS

(71) Applicant: Leaf Healthcare, Inc., Pleasanton, CA (US)

(72) Inventor: Barrett J. Larson, Palo Alto, CA (US)

(73) Assignee: LEAF HEALTHCARE, INC., Pleasanton, CA (US)

( * ) Notice: Subject to any disclaimer, the term of this patent is extended or adjusted under 35 U.S.C. 154(b) by 134 days.

(21) Appl. No.: 15/137,426

(22) Filed: Apr. 25, 2016

(65) Prior Publication Data

US 2016/0310062 A1 Oct. 27, 2016

Related U.S. Application Data

(60) Provisional application No. 62/318,192, filed on Apr. 4, 2016, provisional application No. 62/152,861, filed on Apr. 25, 2015.

(51) Int. Cl.
*A61B 5/04* (2006.01)
*A61B 5/00* (2006.01)
(Continued)

(52) U.S. Cl.
CPC .......... *A61B 5/4362* (2013.01); *A61B 5/0011* (2013.01); *A61B 5/0205* (2013.01);
(Continued)

(58) Field of Classification Search
CPC ....... A61B 5/4362; A61B 5/0011; A61B 5/11; A61B 5/1116; A61B 5/4343;
(Continued)

(56) References Cited

U.S. PATENT DOCUMENTS

| 9,585,614 B2 * | 3/2017 | Dugan ................. A61B 5/0077 |
| 2008/0319353 A1 | 12/2008 | Howell et al. ................. 600/595 |

(Continued)

FOREIGN PATENT DOCUMENTS

| CN | 203303298 U | 11/2013 | ............. A61G 13/12 |
| WO | 2014/192002 A1 | 12/2014 | ............... A41D 1/20 |

(Continued)

OTHER PUBLICATIONS

"Heart Rate Variability: Standards of Measurement, Physiological Interpretation, and Clinical Use," European Heart Journal, vol. 17, pp. 354-381 (28 pages), 1996.

(Continued)

*Primary Examiner* — Rex R Holmes
(74) *Attorney, Agent, or Firm* — Slayden Grubert Beard PLLC

(57) ABSTRACT

Sensor-based systems, devices, and methods are disclosed for monitoring for an aortocaval compression condition in a pregnant woman. A sensor device may be secured directly or indirectly to the woman, which may collect various sensor data related to the woman and/or the fetus. The device may determine a physical orientation of the woman (e.g., upright and/or lateral tilt angles of the woman) and/or biometric parameter(s) of the woman and/or fetus based on the collected sensor data, identify an aortocaval compression condition based on the determined orientation of the woman and/or biometric parameter(s) of the woman and/or fetus, and generate a repositioning alert via an alert mechanism. The disclosed concepts may be implemented, for example, as a personal home-use device, or as a broader system in a hospital or other medical facility, e.g., for monitoring and displaying aortocaval compression related information for multiple patients and/or facilitating patient turn protocols.

11 Claims, 11 Drawing Sheets

(51) Int. Cl.
*A61B 5/0444* (2006.01)
*A61B 5/0205* (2006.01)
*A61B 5/11* (2006.01)
*A61B 5/024* (2006.01)

(52) U.S. Cl.
CPC .............. *A61B 5/0444* (2013.01); *A61B 5/11* (2013.01); *A61B 5/1116* (2013.01); *A61B 5/1118* (2013.01); *A61B 5/1121* (2013.01); *A61B 5/4343* (2013.01); *A61B 5/6823* (2013.01); *A61B 5/6832* (2013.01); *A61B 5/7246* (2013.01); *A61B 5/7275* (2013.01); *A61B 5/7282* (2013.01); *A61B 5/742* (2013.01); *A61B 5/746* (2013.01); *A61B 5/7465* (2013.01); *A61B 5/02405* (2013.01); *A61B 5/02411* (2013.01); *A61B 5/1114* (2013.01); *A61B 2503/02* (2013.01); *A61B 2560/0223* (2013.01); *A61B 2560/0475* (2013.01)

(58) Field of Classification Search
CPC ... A61B 5/7465; A61B 5/0205; A61B 5/6832; A61B 5/7275; A61B 5/6823; A61B 5/7246; A61B 5/1121; A61B 5/7282; A61B 5/742

See application file for complete search history.

(56) References Cited

U.S. PATENT DOCUMENTS

| | | | |
|---|---|---|---|
| 2009/0045966 A1 | 2/2009 | Rocznik | 340/573.7 |
| 2010/0298742 A1 | 2/2010 | Iwasaki et al. | 526/1.71 |
| 2011/0263950 A1 | 10/2011 | Larson et al. | 600/301 |
| 2015/0254956 A1 | 9/2015 | Shen et al. | 340/573.1 |
| 2015/0320339 A1 | 11/2015 | Larson et al. | 600/595 |

FOREIGN PATENT DOCUMENTS

| | | | |
|---|---|---|---|
| WO | 2015/005796 A1 | 1/2015 | A61B 5/024 |
| WO | 2015/062851 A1 | 5/2015 | A61B 5/00 |

OTHER PUBLICATIONS

Bilchick, Kenneth C. et al., "Heart Rate Variability," Journal of Cardiovascular Electrophysiology, vol. 17, No. 6, pp. 691-694, Jun. 1, 2006.

Lweesy, Khaldon et al., "Extraction of Fetal Heart Rate and Fetal Heart Rate Variability from Mother's ECG Signal," International Journal of Medical, Health, Biomedical, and Pharmaceutical Engineering, vol. 3, No. 6, pp. 100-104 (5 pages), 2009.

Mietus, Joseph E. et al., "Heart Rate Variability Analysis with the HRV Toolkit," URL: https://physionet.org/tutorials/hrv-toolkit/, 12 pages, Jan. 23, 2014.

Lamesgin, Gizeaddis et al., "Extraction of Fetal ECG from Abdominal ECG and Heart Rate Variability Analysis," Afro-European Conference for Industrial Advancement. Springer International Publishing, 11 pages, 2015.

De-Giorgio, Fabio et al., "Supine Hypotensive Syndrome as the Probable Cause of Both Maternal and Fetal Death," Journal of Forensic Science, vol. 57, No. 6, pp. 1646-1649 (4 pages), Nov. 26, 2012.

International Search Report and Written Opinion, Application No. PCT/US2016/029163, 12 pages, dated Jul. 15, 2016.

\* cited by examiner

SENSOR-BASED SYSTEMS AND METHODS FOR MONITORING MATERNAL POSITION AND OTHER PARAMETERS

RELATED APPLICATIONS

This application claims priority to U.S. provisional application No. 62/152,861 filed on Apr. 25, 2015 and U.S. provisional application No. 62/318,192 filed on Apr. 4, 2016, the entire contents of which applications are hereby incorporated by reference.

TECHNICAL FIELD

The present disclosure relates in general to the field of sensor-based monitoring systems, and in particular, to sensor-based systems and methods for monitoring a pregnant woman to detect conditions that are not conducive to the health of a developing fetus, e.g., aortocaval compression of the woman, and generating corresponding alarms or notifications.

BACKGROUND

Aortocaval compression is a well-recognized problem that can occur during pregnancy. When pregnant women assume a supine position, the enlarged uterus can compress the maternal aorta and/or inferior vena cava (IVC compression). FIG. 1 illustrates a pregnant woman 1 lying in a non-tilted supine orientation, wherein the uterus 2 carrying the fetus 3 bears on and compresses the maternal aorta and/or inferior vena cava, indicated collectively at 4. This vascular compression can potentially compromise maternal hemodynamics and cause uteroplacental hypoperfusion. This condition, which is often referred to as supine hypotensive syndrome or vena cava syndrome, is not only potentially dangerous to the expectant mother, but can also have devastating consequences to the developing fetus. Since uteroplacental blood flow is directly correlated to maternal perfusion pressure, sustained aortocaval compression can cause fetal hypoxia and acidosis.

To avoid aortocaval compression, women in late pregnancy are often encouraged to adopt a left-lateral tilt position when lying down. The left-lateral tilt position is generally preferred over the right-lateral tilt position, as it has been shown that left-lateral positioning is less likely to cause compression of the inferior vena cava (although lateral tilt in any direction is generally better than supine positioning). For example, FIG. 2A illustrates a pregnant woman 1 lying in a left-lateral tilt position, and FIG. 2B illustrates a cross-section showing the corresponding position of the uterus 2 and fetus 3, wherein the uterus and fetus are shifted laterally with respect to the maternal aorta 5, inferior vena cava 6, and spinal structure 7, thereby relieving aortocaval compression caused by the fetus.

The optimal tilt angle is ultimately dependent on maternal anatomy, gestational age, the position of the fetus within the uterus, and other factors, but it is commonly recommended that a lateral tilt angle of greater than 15 degrees should be used. At lateral tilt angles greater than 15 degrees, aortocaval compression is typically relieved, thereby increasing maternal cardiac output by restoring venous return to the heart.

Recently it has been shown that there is a strong association between maternal sleep position and rates of stillbirth and low birth weight. The first reports of this association were published in 2011 from a case-control study in Auckland. Investigators found that women who slept on their back were 2.5× more likely to have a stillbirth than woman who slept on their left side. These results were confirmed by a 2012 study in Ghana, where investigators found that the supine sleep position increased the probability of a stillbirth by 8× and the probability for low-birth weight by 5×. The findings were confirmed yet again by a 2015 study in Sydney, where investigators found a strong association between supine maternal sleep position and rates of late pregnancy stillbirth.

The association between maternal sleep position and stillbirth is consistent with the fact that aortocaval compression caused by the gravid uterus can impair uteroplacental perfusion and fetal oxygenation. Although significant aortocaval compression can cause maternal hypotension and tachycardia, aortocaval compression can also occur in the absence of any overt changes in maternal vital signs. However, even in the absence of overt vital sign abnormalities, there are measurable biometric signs that can indicate the occurrence of a physiologic derangement, such as caused by aortocaval compression.

It has been demonstrated that characteristic changes in cardiac autonomic nervous system activity occur during pregnancy, which become particularly obvious when pregnant women assume a supine or right lateral decubitus position. To compensate for the decrease in venous return and cardiac output that occurs as a result of aortocaval compression, vagal tone is suppressed and sympathetic tone is enhanced. These autonomic nervous system changes can cause characteristic changes in heart rate or heart rate variability (variation in the beat-to-beat intervals of the heart).

SUMMARY

One embodiment provides a method for monitoring for an aortocaval compression condition of a pregnant user carrying a fetus using a sensor-based monitoring system, wherein the method includes generating sensor signals by one or more sensors of the monitoring system secured directly or indirectly to the user; determining, by a processor of the monitoring system, a physical orientation of the user based on the received sensor signals; identifying, by the processor of the monitoring system, an aortocaval compression condition based at least on the determined physical orientation of the user; automatically generating, by the processor of the monitoring system, an alert in response to identifying the aortocaval compression condition; and outputting the alert to the user via an alert mechanism.

In one embodiment, identifying an aortocaval compression condition based at least on the determined physical orientation of the user comprises determining at least one value representing the determined physical orientation of the user; comparing the at least one value to at least one threshold value; and identifying an aortocaval compression condition based at least on the results of the comparison.

In one embodiment, threshold values are manually selected.

In one embodiment, threshold values are automatically determined and/or adjusted by the monitoring system based on at least one of sensor data, historical data, or user data.

In one embodiment, the method includes determining or accessing from memory at least one other parameter related to the user or the fetus; and identifying the aortocaval compression condition based at least on (a) the determined physical orientation of the user and (b) the at least one other parameter related to the user or the fetus.

In one embodiment, the at least one other parameter related to the user or the fetus comprises at least one of a pregnancy stage, a gestational age of the fetus, a health status of the user, a health status of the fetus, a heart rate or heart rate variability of the user, a heart rate or heart rate variability of the fetus, an electrocardiogram (EKG) signal of the user, an EKG signal of the fetus, data regarding activity or ambulation of the user, or other biometric parameters of the user or fetus.

In one embodiment, the step of identifying the aortocaval compression condition based at least on (a) the determined physical orientation of the user and (b) the at least one other parameter related to the user or the fetus comprises: determining an orientation value representing the determined physical orientation of the user; determining a physical orientation threshold value as a function of the at least one other determined parameter related to the user or the fetus; comparing the orientation value to the physical orientation threshold value; and identifying an aortocaval compression condition based at least on the results of the comparison.

In one embodiment, determining the at least one other parameter related to the user or the fetus comprises determining at least one biometric parameter of at least one of the user or the fetus based on the received sensor signals; and determining a physical orientation threshold value as a function of the at least one other determined parameter related to the user or the fetus comprises: accessing a variable threshold equation or algorithm stored in the memory, the variable threshold equation or algorithm defining a relationship between the physical orientation threshold value and the determined at least one biometric parameter; and applying the variable threshold equation or algorithm to calculate the physical orientation threshold value based on the determined at least one biometric parameter.

In one embodiment, the method includes generating a series of time-based correlations between instances of the determined orientation value of and instances of the at least one other determined parameter related to the user or the fetus; identifying one or more instances of the at least one other determined parameter associated with an instance of an aortocaval compression condition; identifying one or more instances of the orientation value correlated with the identified one or more instances of the at least one other determined parameter; and automatically adjusting the physical orientation threshold value based on the identified one or more instances of the orientation value.

In one embodiment, the step of identifying the aortocaval compression condition based at least on (a) the determined physical orientation of the user and (b) the at least one other parameter related to the user or the fetus comprises: determining a parameter value representing the at least one other parameter related to the user or the fetus; determining a parameter threshold value as a function of the determined physical orientation of the user; comparing the parameter value to the parameter threshold value; and identifying an aortocaval compression condition based at least on the results of the comparison.

In one embodiment, determining the at least one other parameter related to the user or the fetus comprises determining at least one biometric parameter of at least one of the user or the fetus based on the received sensor signals; and determining a parameter threshold value as a function of the determined physical orientation of the user comprises: accessing a variable threshold equation or algorithm stored in the memory, the variable threshold equation or algorithm defining a relationship between the parameter threshold value and the physical orientation of the user; and applying the variable threshold equation or algorithm to calculate the parameter threshold value based on the determined physical orientation of the user.

In one embodiment, determining a physical orientation of the user based on the received sensor signals comprises determining a lateral tilt angle of the user based on the received sensor signals; and the variable threshold equation or algorithm defines a relationship between the parameter threshold value and the lateral tilt angle of the user.

In one embodiment, determining a physical orientation of the user based on the received sensor signals comprises determining at least one of an upright tilt angle or a lateral tilt angle; and identifying an aortocaval compression condition based at least on the determined physical orientation of the user comprises comparing the at least one of the upright tilt angle or the lateral tilt angle with a corresponding threshold angle value.

In one embodiment, the monitoring system comprises a self-contained device including the one or more sensors and the processor.

In one embodiment, the method includes positioning the self-contained monitoring system proximate the user's umbilicus.

In one embodiment, identifying an aortocaval compression condition based at least on the determined physical orientation of the user comprises: calculating a metric representing a probability of an aortocaval compression condition; comparing the metric representing a probability of an aortocaval compression condition to a threshold value; and identifying an aortocaval compression condition if the metric exceeds the threshold value.

In one embodiment, the step of identifying an aortocaval compression condition based at least on the determined physical orientation of the user comprises: determining an activity level of the user based on the received sensor signals; and identifying the aortocaval compression condition based at least on the determined physical orientation of the user and the determined activity level of the user.

In one embodiment, the step of identifying an aortocaval compression condition based at least on the determined physical orientation of the user comprises: determining an activity level of the user based on the received sensor signals; determining at least one biometric parameter of at least one of the user and the fetus based on the received sensor signals; and identifying the aortocaval compression condition based at least on (a) the determined physical orientation of the user, (b) and the determined activity level of the user, and (c) the determined at least one biometric parameter.

In one embodiment, the step of determining a physical orientation of the user based on the received sensor signals comprises determining an upright tilt angle and a lateral tilt angle; and the step of identifying the aortocaval compression condition based at least on (a) the determined physical orientation of the user, (b) and the determined activity level of the user, and (c) the determined at least one biometric parameter comprises (i) performing a plurality of comparisons including: comparing the determined upright tilt angle with an upright tilt angle threshold; comparing the determined lateral tilt angle with a lateral tilt angle threshold; comparing the determined activity level with an activity level threshold; comparing the determined at least one biometric parameter with at least one biometric parameter threshold; and (ii) identifying the aortocaval compression condition based at least on the plurality of comparisons.

In one embodiment, the method further includes communicating aortocaval compression related information of the user from the monitoring system to a remote display device, wherein the aortocaval compression related information comprises at least one of: information indicating the determined physical orientation of the user, information indicating the identification of the aortocaval compression condition, or information indicating at least one other parameter determined by the processor based on the received sensor signals.

In one embodiment, the method further includes receiving, at the remote display device, the aortocaval compression related information of the user and aortocaval compression related information of at least one other user; and displaying, by the remote display device, the aortocaval compression related information of the user and the at least one other user.

Another embodiment provides a method for monitoring for an aortocaval compression condition in a plurality of users by a system including a sensor-based monitoring device associated with each user and a common display or alert device. The method includes monitoring for an aortocaval compression condition in each respective user by generating sensor signals by one or more sensors of the monitoring device associated with the respective user; automatically determining a physical orientation of the respective user based on the sensor signals; and automatically determining the presence of an aortocaval compression condition based at least on the determined physical orientation of the user. The method further includes communicating aortocaval compression related information for each user from the sensor-based monitoring device associated with each respective user to the common display or alert device, wherein the aortocaval compression related information for each user comprises at least one of: information indicating the determined physical orientation of the respective user, information indicating the determination of an aortocaval compression condition, or information indicating at least one other parameter determined by the respective monitoring device based on the sensor signals generated by the one or more sensors of the respective monitoring device. The method further includes the common display or alert device displaying the received aortocaval compression related information for one or more of the plurality of users and/or generating an alert in response to receiving information indicating an aortocaval compression condition in one or more users.

In one embodiment, the common display or alert device is located in a hospital or other medical facility.

Another embodiment provides a monitoring system for monitoring for an aortocaval compression condition, the monitoring system comprising: one or more sensors configured to be secured directly or indirectly to the user and configure to generate sensor signals; a processor; computer instructions stored in non-transitory computer-readable medium and executable by the processor to determine a physical orientation of the user based on the received sensor signals, identify an aortocaval compression condition based at least on the determined physical orientation of the user, and automatically generate and transmit an alert signal in response to identifying the aortocaval compression condition; and an alert mechanism configured to receive the alert signal and output an alert to the user.

In one embodiment, the monitoring system includes a self-contained device including the one or more sensors, the processor, and the non-transitory computer-readable medium storing the computer instructions.

Another embodiment provides a system for monitoring for an aortocaval compression condition in a plurality of users, including a plurality of sensor-based monitoring devices, each associated with a respective user, and a common display or alert device communicatively coupled to each sensor-based monitoring device. Each sensor-based monitoring device associated with a respective user may include one or more sensors configured to generate sensor signals associated with the respective user; a processor; computer instructions stored in non-transitory computer-readable medium and executable by the processor to: receive the sensor signals generated by the one or more sensors; determine a physical orientation of the respective user based on the received sensor signals; and determine the presence of an aortocaval compression condition based at least on the determined physical orientation of the respective user; and a transmission device configured to communicate aortocaval compression related information regarding the respective user to the common display or alert device, wherein the aortocaval compression related information comprises at least one of: information indicating the determined physical orientation of the respective user, information indicating the determination of an aortocaval compression condition, or information indicating at least one other parameter determined by the sensor-based monitoring device based on the received sensor signals. The common display or alert device is configured to receive aortocaval compression related information regarding the plurality of users from the sensor-based monitoring device associated with each respective user, and to display the received aortocaval compression related information regarding one or more of the plurality of users and/or generate an alert in response to receiving information indicating an aortocaval compression condition in one or more of the users.

In one embodiment, the common display or alert device is located in a hospital or other medical facility.

BRIEF DESCRIPTION OF THE DRAWINGS

The accompanying figures, which are included as part of the present specification, illustrate example embodiments of the present disclosure and together with the general description given above and the detailed description of such embodiments provided below serve to explain and teach the principles described herein.

Figure 1:
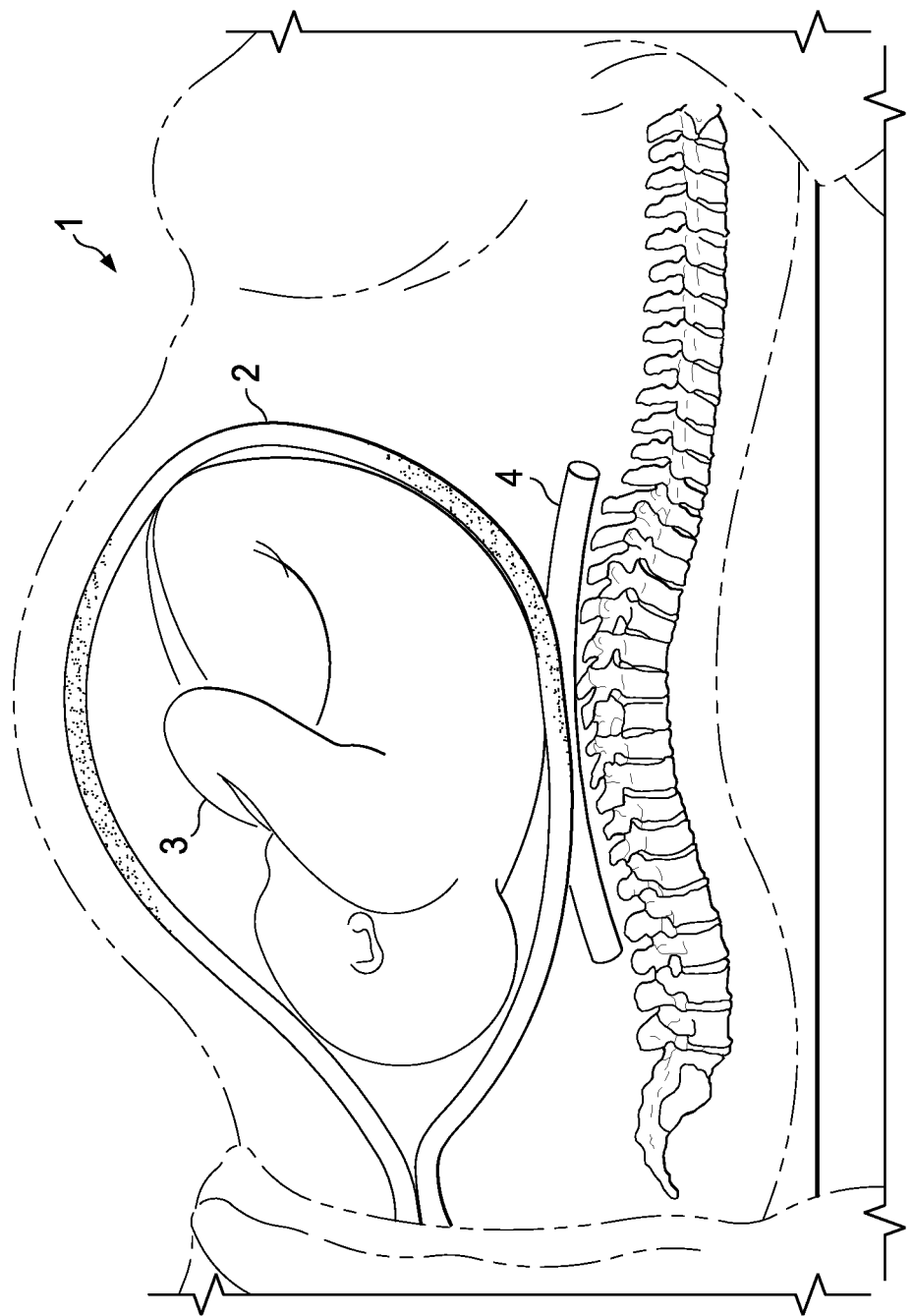
FIG. 1 illustrates an aortocaval compression resulting from a pregnant woman being oriented in a non-tilted supine position.
Figure 2A:
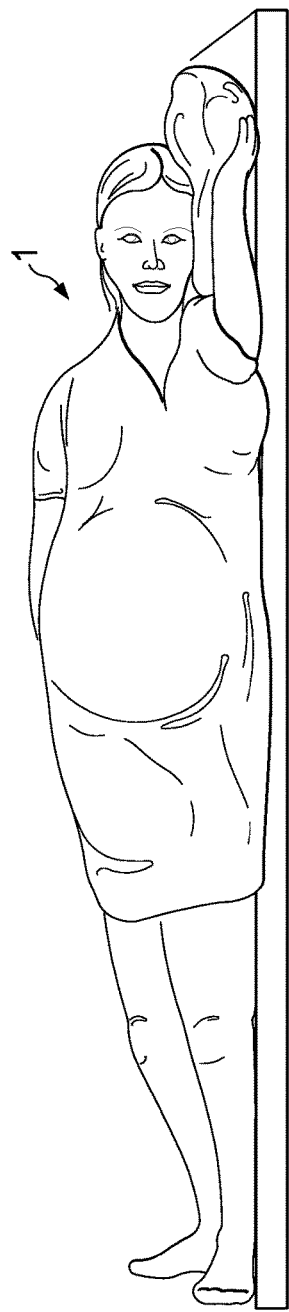
FIG. 2A illustrates a pregnant woman oriented with a lateral tilt, which may relieve the aortocaval compression condition shown in FIG. 1.
Figure 2B:
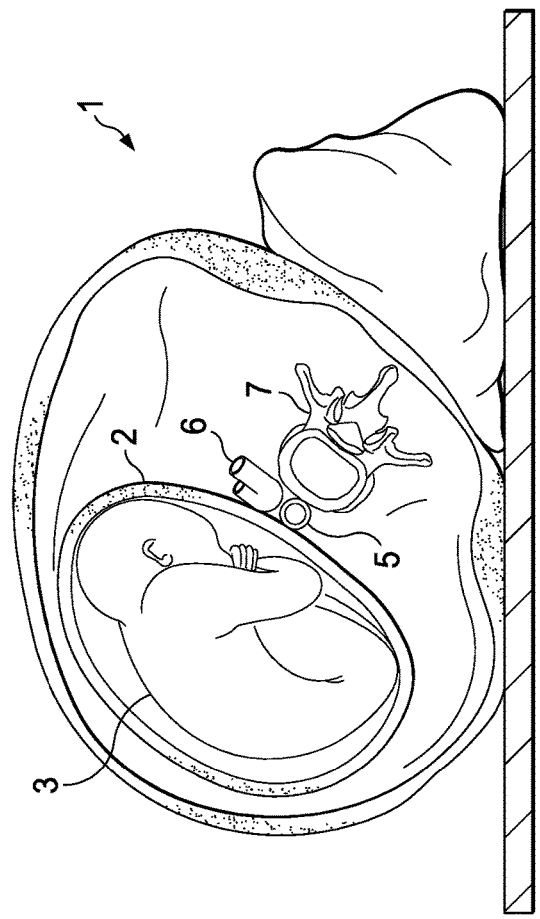
FIG. 2B is a cross-section of the laterally tilted orientation shown in FIG. 2A, illustrating the laterally-shifted position of the fetus with respect to the maternal aorta and inferior vena cava, thereby relieving the aortocaval compression condition.

The figures are not necessarily drawn to scale and elements of similar structures or functions are generally represented by like reference numerals for illustrative purposes throughout the figures. The figures are only intended to facilitate the description of the various embodiments described herein. The figures do not describe every aspect of the teachings disclosed herein and do not limit the scope of the claims.

DETAILED DESCRIPTION

Systems, devices, and methods are disclosed for detecting and notifying a pregnant woman (also referred to herein as a "user") of an aortocaval compression condition, e.g., due to the physical orientation of the woman (e.g., lying prone), which may compromise blood flow to the developing fetus. In particular, some embodiments provide a sensor-based monitoring system that is secured to the user, e.g., at or near the umbilicus, which includes sensor(s) configured to sense the physical orientation of the user (e.g., including tilt angles), biometric parameters of the user and/or fetus, and/or other relevant parameters, a processor and software for analyzing such sensed information to identify an aortocaval compression condition, and an alert mechanism to notify the user of the aortocaval compression condition or other relevant information. The sensor(s) may be configured to detect an orientation of the user (which may include one or more orientation parameters, such as the user's upright tilt angle and lateral tilt angle), ambulation of the user, one or more biometric parameters of the user and/or the fetus (e.g., heart rate, heart rate variability, EKG signals), environmental parameters (e.g., temperature, humidity, etc.), and/or other parameters.

As used herein, reference to a sensor measuring or detecting a parameter, such as orientation, upright tilt angle, lateral tilt angle, ambulation, heart rate, heart rate variability, etc. refers to a sensor generating sensor signals in response to some interaction with the user and/or fetus and a processor (integrated with or discrete from the sensor itself) processing the sensor signals to determine or calculate a parameter value or value(s).

As used herein, an "aortocaval compression condition" refers to a condition of a pregnant woman in which the maternal aorta and/or inferior vena cava are compressed, e.g., by the gravid uterus, by a degree or extent that is harmful or potentially harmful to the health of the pregnant woman and/or fetus, as would be generally understood by those in the field. As used herein, references to identifying or determining the presence of an aortocaval compression condition (or simply, identifying an aortocaval compression condition) refer to identifying or determining the presence of one or more characteristics (e.g., individually or in combination) of a pregnant woman and/or fetus having a correlation with a potential or existing aortocaval compression condition (e.g., a particular degree of aortocaval compression) of the pregnant woman. In some embodiments, identifying the presence of an aortocaval compression condition involves analyzing sensor-based signals and/or other relevant information with respect to one or more metrics (e.g., threshold value(s)) that are predefined for the respective system, device, or method as having a correlation with a potential or existing aortocaval compression condition.

In some embodiments, system 10 explicitly calculates a probability of the presence of an aortocaval compression condition, and determines an alarm condition (and/or a severity of alarm condition) based on the explicitly calculated probability of aortocaval compression condition, e.g., by comparing the determined probability to one or more threshold values. In other embodiments, system 10 is configured to determine the presence (or not) of an aortocaval compression condition (and/or a severity level of aortocaval compression condition) by executing an algorithm that does not explicitly calculate a probability of aortocaval compression, but which inherently incorporates or represents an evaluation of the probability of an aortocaval compression condition, e.g., wherein such probability metrics or limits may be embodied by the threshold value(s) utilized in such algorithm. Thus, it should be understood that identifying or determining the presence of an aortocaval compression condition may or may not include an explicit determination of a probability of aortocaval compression.

To illustrate some of the concepts discussed above, a wearable sensor-based monitoring device according to an example embodiment may store equation(s) or look-up table(s) that define an aortocaval compression condition as a function of three variables measured based on sensor signals (upright tilt angle of the user, lateral tilt angle of the user, and heart rate variability of the user). The monitoring device may thus identify an aortocaval compression condition (or no aortocaval compression condition) based on the three measured variables and the stored equation(s) or look-up table(s), and output an alarm if an aortocaval compression condition is identified. Thus, it should be understood that an aortocaval compression condition (as used herein) is defined by, programmed into, accessible by, or otherwise associated with each respective system, device, or method, such that different instances of systems, devices, or methods according to the invention may be designed to identify an aortocaval compression condition based on one or more different characteristics or parameters (e.g., a device according to one embodiment may identify an aortocaval compression condition based on lateral tilt angle and user's heart rate, while a device according to another embodiment may identify an aortocaval compression condition based on lateral tilt angle, upright tilt angle, activity level of the user, and heart rate variability of the user), or based on different values of the same characteristics or parameters (e.g., a device according to one embodiment may identify an aortocaval compression condition based on lateral tilt angle of <15 degrees combined with a user heart rate above 80, while a device according to another embodiment may identify an aortocaval compression condition based on lateral tilt angle of <10 degrees combined with a user heart rate of above 75).

Some embodiments provide increased sensitivity and/or accuracy in identifying an aortocaval compression condition, e.g., as compared with existing systems and methods, which are often susceptible to high rates of false positive and false negative alerts. False positive alerts may unnecessarily disrupt the user's sleep and cause unwarranted distractions, while false negative alerts may put the health of the woman and/or fetus at risk.

Figure 3:
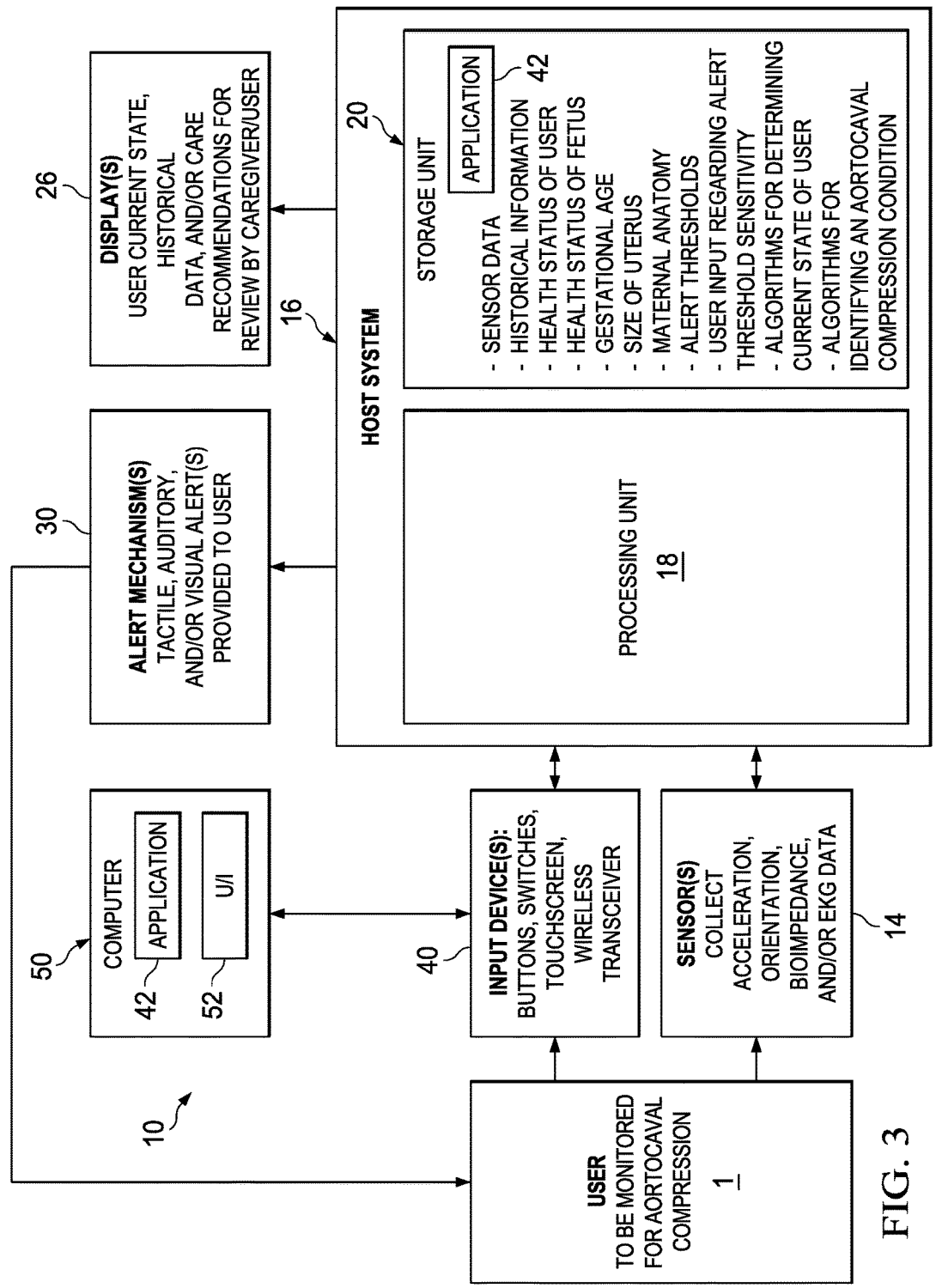
FIG. 3 illustrates an example sensor-based system for monitoring for the presence of aortocaval compression in a pregnant woman, according to one embodiment.
Figure 11:
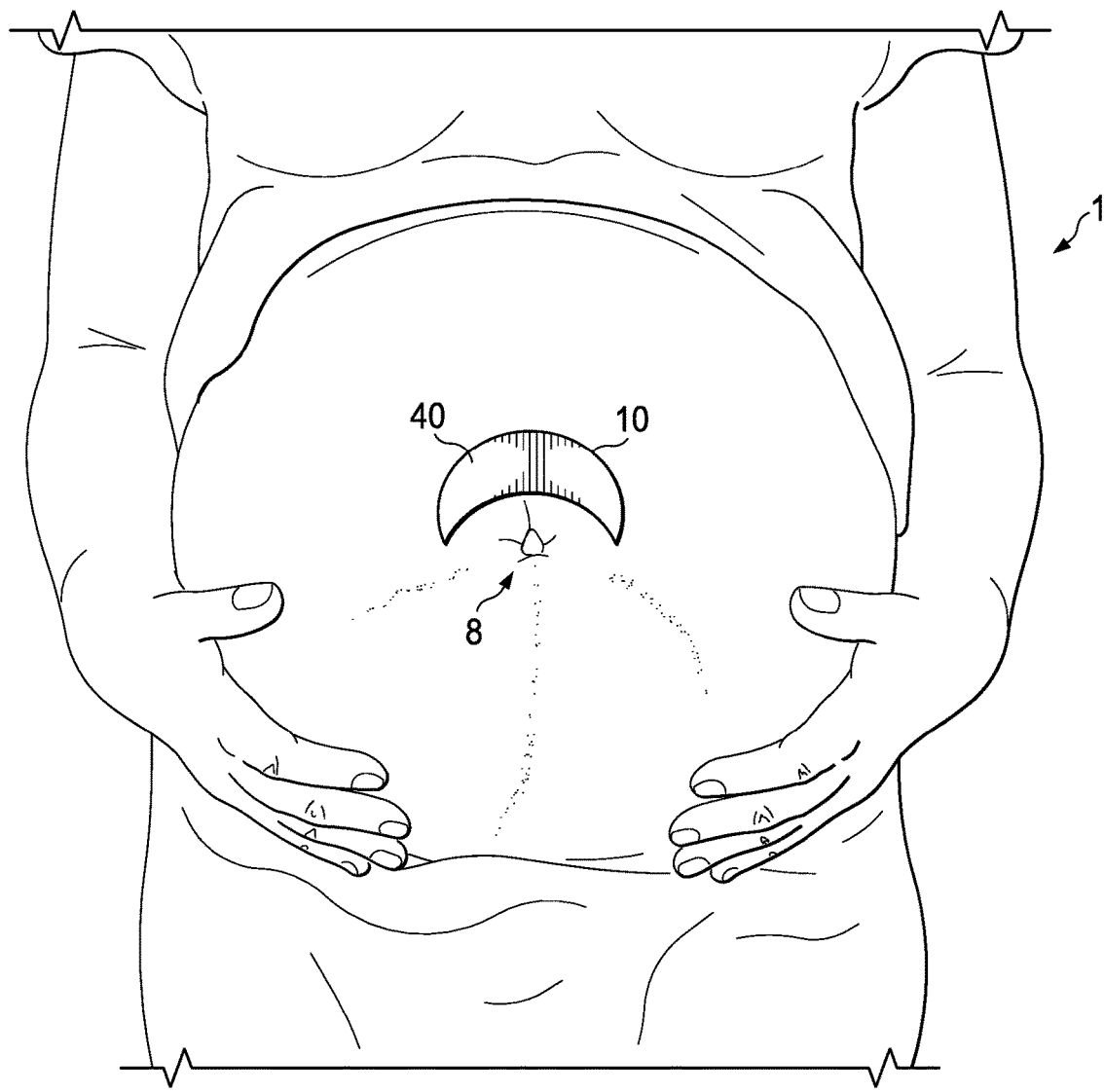
FIG. 11 illustrates an example crescent-shaped sensor oriented with respect to the umbilicus, for monitoring for the presence of aortocaval compression in a pregnant woman, according to one example embodiment.

FIG. 3 illustrates an example monitoring system 10 for monitoring for the presence of aortocaval compression in a user 1, e.g., a pregnant woman, according to some embodiments. As shown, monitoring system 10 may include one or more sensors 14, a host system 16 including at least one processor 18, at least one storage unit 20, at least one display device 26, at least one alert mechanism 30, at least one input device 40, and/or an application 42. In some embodiments, monitoring system 10 may include a self-contained device including sensor(s) 14, host system 16, display(s) 26, and alert mechanism(s) 30 arranged within a device housing configured to be secured directly or indirectly to the user, with the sensor(s) 14 arranged in the housing for suitable interaction with the user. FIG. 11 (discussed in more detail below) shows an example of a self-contained monitoring system 10 having a housing 40 configured to be secured to the user (e.g., adhesively) near the umbilicus.

In other embodiments, the components of monitoring system 10 shown in FIG. 3 may be split between two or more separate systems, devices, or housings. For example, system 10 may include a sensor device including sensor(s) 14 and alert mechanism(s) 30 arranged in a housing configured to be secured directly or indirectly to the user, and an analytics device including host system 16 and display(s) 26 arranged in a housing separate from the sensor device, wherein the two components may be communicatively connected via wireless link (e.g., RF, Bluetooth, WiFi, or other wireless communications protocol) or via a wired link. As another example, system 10 may include a sensor device including sensor(s) 14, host system 18, and alert mechanism(s) 30 arranged in a self-contained housing configured to be secured directly or indirectly to the user, with display device 26 being distinct from but communicatively connected to the self-contained sensor device via wireless or wired link. In such embodiments, display device 26 may be a stand-alone display device of system 10, or may be a display of an existing computer (e.g., laptop, desktop, tablet, smartphone, etc.) Thus, in such embodiments, the sensor device may communicate data to the associated display device 26 or existing computer, e.g., via wireless communication link, for display of such data.

In view of the above, references herein to a "sensor device" refer to the module, housing, or component of system 10 that includes sensor(s) 14, e.g., the full system 10 in embodiments in which system 10 is embodied as a self-contained sensor device (e.g., as shown in FIG. 11) or the module, housing, or component of a multi-component system 10, e.g., as the example two-component embodiments of system 10 discussed above.

Thus, regardless of the respective arrangement of the system components within one or multiple housings, the respective sensor device of housing 10 may be configured to be directly or indirectly secured to the user, e.g., in a manner that maintains the sensor device in a stationary location with respect to the user's body, e.g., with respect to the user's umbilicus, once the sensor device is applied. For example, the sensor device may be adhesively attached to the skin near the umbilicus, or alternatively may be stitched into, contained within a pocket, or otherwise secured to an item of clothing or garment (e.g., strap, band, or other garment) configured to be worn by the user and configured to maintain the sensor device in a stationary location with respect to the user's body, e.g., with respect to the user's umbilicus or other known anatomic reference point. In some embodiments, the sensor device may be a lightweight, disposable sensor that attaches to the user via an adhesive backing of the sensor device.

Sensor(s) 14 may include one or more sensors configured to interact with the user and/or fetus and generate sensor signals based on such interaction. Sensor(s) 14 may include any one or more types of sensors, and one or more instances of each type of sensor. For example, sensor(s) 14 may include (a) one or more single-axis or multi-axis orientation sensors (e.g., for determining the lateral tilt angle and upright tilt angle of the uterus and/or other orientation of the user) and/or (b) one or more bioimpedance sensors, EKG electrodes, and/or other biometric sensors (e.g., for measuring maternal and/or fetal heart rate and heart rate variability), and/or (c) any other type(s) and number of sensors for detecting characteristics of the user, fetus, and/or environment. Orientation sensors(s) may include accelerometer(s), inclinometer(s), angle gauge(e), or any other sensor(s) that generate signals regarding single-axis or multi-axis orientation. In some embodiments, an orientation sensor (e.g., accelerometer) may be used for detecting both an orientation of the user and one or more other parameters, e.g., breathing (and thus, breath rate), pulse (and thus, heart rate and/or heart rate variability), activity level of the user, etc.

One embodiment includes a single sensor is used to monitor the orientation of a pregnant woman (and/or additional parameters, e.g., heart rate, heart rate variability, activity level of the user). Other embodiments include multiple different types of sensors to provide multiple types of input for identifying an aortocaval compression condition, or multiple instances of the same type of sensor, e.g., for providing redundancy. In some embodiments, system 10 may include two or more spatially separated orientation sensors, e.g., arranged in the same sensor device or in two or more discrete sensor devices of the same system 10, which can be used for determining or estimating the curvature of the body in the area of the sensors.

Host system 16 may include a processing unit 18 including at least one processor and a storage unit 20 including at least one non-transitory memory device. Processing unit 18 may include any number and type(s) of microprocessor, microcontroller, or other device(s) for processing sensor signals. Storage unit 20 may include any number and type(s) of non-transitory memory or data storage devices, e.g., Random Access Memory (RAM), flash memory, Read Only Memory (ROM), Electrically Programmable ROM (EPROM), Electrically Erasable Programmable ROM (EEPROM), registers, a hard drive, a removable drive (e.g., thumb drive), etc.

Host system 16 is communicatively coupled to sensor(s) 14 by wired or wireless link(s), such that processing unit 18 is configured to receive sensor signals generated by sensor(s) 14 and process such sensor signals based on algorithm(s), look-up table(s), threshold(s), and/or other data accessed from storage unit 20 to identify an aortocaval compression condition, and generate and communicate alert signals to alert mechanism(s) 30 as appropriate.

Storage unit 20 may store any algorithm(s), look-up table(s), threshold(s), and/or other data associated with the pregnant woman and/or fetus relevant for identifying an aortocaval compression condition. For example, storage unit 20 may store any of the following:

software, firmware, or other computer instructions executable by processing unit 18 to perform any of the various functions of system 10 disclosed herein;

non-sensor-based data, e.g., information regarding the status or health of the user and/or fetus, e.g., health status of the user, health status of the fetus, age of the user, gestational age of the fetus, size of the uterus, characteristics or metrics of the user's anatomy, known fetal anomalies, or other non-sensor-detected data (non-sensor-based data may be manually entered by the user or otherwise programmed in memory 20);

historical data collected by system 10, e.g., historical sensor-based data (e.g., regarding the orientation, activity level, biometrics, electrocardiographic data, heart rate, heart rate variation, etc. of the user and/or fetus over time), historical determinations/identifications of aortocaval compression conditions, and/or other alert determinations determined by system 10 over time;

e.g., historical information regarding the orientation, activity level, heart rate, heart rate variation, etc. of the user and/or fetus over time, as determined by system 10;

algorithms/look-up tables for determining orientation information based on sensor signals (e.g., signals from one or more orientation sensors), e.g., algorithms for calculating upright tilt angle (e.g., of the uterus) and/or lateral tilt angle (e.g., of the uterus) based on orientation sensor signals;

algorithms/look-up tables for determining or calculating heart rate and/or heart rate variability of the woman and/or the fetus based on sensor signals from an orientation sensor, bioimpedance sensor, or EKG electrodes;

algorithms/look-up tables for determining or calculating ambulation or other activity level of the woman;

threshold values for one or more various parameters, e.g., an upright tilt angle threshold, a lateral tilt angle threshold, an ambulation threshold, an activity level threshold, a heart rate threshold, a heart rate variability threshold, low battery threshold value, alert thresholds values, etc.;

algorithms/look-up tables for determining and/or adjusting one or more threshold values based on specified sensor-based data, non-sensor-based data, and/or historical data;

user input regarding alert preferences;

algorithms/look-up tables for identifying the presence of an aortocaval compression condition and/or for determining a severity level of aortocaval compression condition based on sensor-based and/or other input data; and/or algorithms/look-up tables for determining a probability of an aortocaval compression condition and/or a severity level of aortocaval compression condition based on sensor-based and/or other input data.

Non-sensor-based data may be manually entered by the user or otherwise programmed in storage unit 20. Further, in alternative embodiments, one or more types of non-sensor-based data listed above may be automatically determined by system 10 based on sensor signals from sensor(s) 14. For example, in some embodiments, system 10 may be configured to determine the gestational age of the fetus, size of the uterus, and/or particular characteristics or metrics of the user's anatomy (e.g., curvature of the abdomen) based on signals from sensor(s) 14.

Display device(s) 26 may include any device configured to display information to the user or other person, e.g., one or more display screens or monitors (e.g., LED, LCD, etc.), lights, lighted text/icons, or other device for displaying information to a person. Each display device 26 may be integrated in the respective sensor device (e.g., as part of a self-contained system 10), or may be distinct and/or remote from the sensor device, e.g., a stand-alone display device of system 10, or a display devices of an existing computer system (e.g., laptop, desktop, tablet, smartphone, etc.). As discussed in more detail below, some embodiments include one or more remote display devices 26 suitable for viewing by a caregiver, e.g., one or more monitors or screens located in or near a nurse station or other common area, or a display device of a portable computer, laptop, tablet, smartphone, or other computer device carried by or accessible to a caregiver, e.g., doctor, nurse, etc.

Alert mechanism(s) 30 may include any device configured to communicate one or more human-perceptible alerts or notifications to the user. Alerting mechanisms may be auditory, visual, or tactile in nature. For example, alert mechanism(s) 30 may include a vibration unit; a speaker, buzzer, or any other tactile, auditory, and/or visual alert/notification device. In some embodiments, alert mechanism(s) 30 may comprise display device 26, for visually displaying alerts/notifications to the user.

As with display devices 26 discussed above, some embodiments include one or more remote alert mechanisms 30, e.g., for providing alerts to a caregiver, e.g., a doctor, nurse, or other caregiver. For example, alert mechanisms 30 may include any device configured to provide any suitable auditory, visual, or tactile alert to a person or at a location remote from the monitored user, e.g., a visual or audible alarm located near a nurse station or other common area of a medical or care facility, or a visual or audible alarm output by a portable computer, laptop, tablet, smartphone, or other computer device carried by or accessible to a caregiver, e.g., doctor, nurse, etc.

In one embodiment, an alert mechanism provides haptic feedback via a vibration. Once the alert condition has been resolved, the haptic vibration discontinues. System 10 may modulate one or more properties of the haptic feedback (strength, pulse duration, pulse interval, etc.) based on the severity of the alert. For example, if system 10 identifies a severe alert condition, system 10 may maintain the haptic vibration at maximum intensity for an extended duration. However, if system 10 identifies a relatively minor alert condition, system 10 may provide haptic vibration at a relatively low intensity with a brief pulse duration and long pauses between pulses. As the severity of the alert condition changes, system 10 may adjust one or more parameters of the haptic feedback accordingly. The process of modifying parameter(s) of the alert mechanism based on the severity of the alert condition can be applied to any form of user feedback, including all forms of visual, auditory, and tactile feedback, for example.

Input devices 40 may include any devices or elements for receiving input from a user or other person (e.g., caregiver). For example, input devices may include one or more buttons, switches, sliders, etc. provided on the sensor device for allowing a user to manually provide input to system 10. In one embodiment, the sensor device may include one or more buttons, switches, sliders, etc., along with a display (e.g., LCD screen) or series of lights (e.g., LEDs) and suitable software that defines a user input system allowing a user to navigate and select various operational parameters and/or characteristics of the user and/or fetus, e.g., via a multi-level menu. In other embodiments, input device 40 may include a wireless receiver or transceiver configured to communicate (via wireless and/or wired communications) with an application 42 hosted by or accessible at a computer 50. Computer 50 may be a laptop, tablet, smartphone, or any other type of computer. Application 42 may display various operational settings and/or characteristics or parameters of the respective user and/or fetus, and allow a person (e.g., the user, a caregiver, or other person) to input, set, or adjust such settings, characteristics, or parameters via any suitable user interface device(s) 52 provided by computer 50 (e.g., keyboard, mouse, touchscreen, etc.). In other embodiments, application 42 may be stored in host system 16, as shown in FIG. 3. In other embodiments, applications 42 may be located at both host system 16 and a remote computer 50, with each application 42 providing relevant functionality for interfacing with a user and communicating with the other system components.

Regardless of the embodiment, the input device 40 may define a user input system that allows a user to select one or more operational parameters such as detection sensitivity level, alert threshold values, alarm mode, or alarm intensity, for example, and/or one or more characteristics or parameters of the user and/or fetus, such as maternal age, gestational age, due date, maternal health, fetal health, or number of prior pregnancies, for example.

Implementation in a Hospital, Clinic, or Other Medical or Care Facility

In some embodiments, system 10 may be configured for implementation in a hospital, clinic, or other medical or care facility, and may include, or be configured to communicate data to, one or more display devices 26 remote from the sensor device secured to the user (which sensor device may also include onboard display device(s) 26). For example, as mentioned above, such remote display devices 26 may include one or more monitors or screens located for convenient viewing by caregiver(s) (e.g., monitors located in or near a nurse station or other common area). As another example, remote display devices 26 may include portable computers, laptops, tablets, smartphones, or other computer devices carried by or accessible to caregivers, e.g., doctors, nurses, etc.

In some embodiments, each remote display device 26 is configured to display data received from multiple sensor devices secured to and monitoring multiple different users, such that a caregiver can monitor multiple users on one display device 26. For example, a remote display device 26 may simultaneously display relevant status information for each of multiple users being monitored by respective sensor device, e.g., sensor-based status data determined by the processing unit 18 of each respective sensor device. As another example, a remote display device 26 may selectively display data regarding one of multiple users being monitored, e.g., upon selection of each respective user by a caregiver via a computer connected to the display device 26. Thus, such remote display devices 26 may include any suitable communication devices and processing resources to receive data from multiple sensor devices and process such data to display information regarding multiple different users being monitored for aortocaval compression conditions.

The following co-pending U.S. patent applications (as of the date of filing of the present application) disclose various features and concepts for monitoring and displaying status information related to the orientation or position of users/patients for the prevention of pressure ulcers and other conditions: (a) U.S. application Ser. No. 12/730,663, filed Mar. 24, 2010, entitled "Patient Movement Detection System and Method"; (b) U.S. application Ser. No. 13/070,189, filed Mar. 23, 2011, entitled "Systems, Devices, and Methods for Preventing, Detecting, and Treating Pressure-Induced Ischemia, Pressure Ulcers, and Other Conditions"; (c) U.S. application Ser. No. 14/244,720, filed Apr. 3, 2014, entitled "System and Method for Analyzing Patient Orientation, Location and Movement"; and (d) U.S. application Ser. No. 14/543,887, filed Nov. 14, 2014, entitled "Systems, Devices, and Methods for the Prevention, and Treatment of Pressure Ulcers, Bed Exits, Falls, and Other Conditions" (collectively, "Co-Pending Position Monitoring and Display Applications")

In some embodiments, system 10 may incorporate any of the features and concepts for monitoring and displaying status information regarding multiple users as disclosed in any of the Co-Pending Position Monitoring and Display Applications. Thus, the portions of the Co-Pending Position Monitoring and Display Applications that relate to the monitoring and display of status information regarding user/patients (e.g., multiple users/patients) via a remote display device, e.g., a screen or monitor located in a common caregiver area of a hospital, clinic, or other medical or care facility are hereby incorporated.

For example, implementing the relevant features and concepts disclosed in the Co-Pending Position Monitoring and Display Applications, a display device 26 of or associated with monitoring system 10 may be configured to display various identification information, status information, and/or alarm information for each of one or more monitored users, e.g., (a) an identifier for each respective user (e.g., a room number, user name, or anonymous or partially anonymous user identifier); (b) whether the respective user is generally upright, sitting, or prone (and if prone, whether the user is tilted to the left or right), (c) one or more tilt angles, e.g., upright tilt angle, left-side lateral tilt angle, and right-side lateral tilt angle, for example, (d) a duration that the user has been in the current orientation, (e) whether an aortocaval compression condition is currently detected and if so, a duration of the ongoing aortocaval compression condition, (f) instructions or recommendations for turning or repositioning the user (e.g., to relieve an ongoing aortocaval compression condition), (g) information regarding a user repositioning protocol being implemented for the user, and/or (h) any other relevant information.

System Operation

As discussed above, system 10 is operable to monitor for an aortocaval compression condition and, upon identifying such condition, communicate an alert or notification to the user, such that user may take action to alleviate the aortocaval compression condition, e.g., by assuming a suitable left-side lateral tilt angle. Sensor(s) 14 generate sensor signals, which are communicated to processing unit 18 for processing. Processing unit 18 analyzes the received sensor signals based on algorithms, look-up tables, thresholds, non-sensor-based data, historical data, and/or other data stored in storage unit 20 to identify an aortocaval compression condition and/or other alert condition, and generates and communicates corresponding alert or notification signals to display device(s) 26 and/or alert mechanism(s) 30, which communicate the alert or notification to the user.

In some embodiments, system 10 uses an orientation sensor (e.g., a multi-axis accelerometer) 14, together with a microcontroller 18 and an alert mechanism 30 to notify the user if the uterus is in a position/orientation that could be compromising maternal hemodynamics, uteroplacental blood flow, or fetal oxygenation. In other embodiments, system 10 further includes a bioimpedance sensor or EKG electrodes, such that the maternal and/or fetal heart rate and heart rate variability can be analyzed. This electrical data can be used independently, or in conjunction with orientation sensor data, to make determinations as to the probability of aortocaval compression and the requirement for repositioning. In some embodiments, the sensor device is a lightweight, disposable device that is associated to the user in a known orientation and position relative to the uterus, e.g., at the umbilicus. The sensor can be secured to the user by an adhesive or other suitable attachment mechanism that maintains a constant position and orientation of the sensor with respect to the user over time. In some embodiments, the sensor may be incorporated into a garment or strap that is worn by the user.

As mentioned above, aortocaval compression typically occurs when a pregnant woman lies in the supine position. As the upright tilt angle of the uterus increases, such as occurs when transitioning from supine to standing, the probability for aortocaval compression decreases. Furthermore, as the lateral tilt angle of the uterus increases, especially a left-side tilt angle, the probability for aortocaval compression decreases. Thus, some embodiments determine the upright tilt angle and/or lateral tilt angle of the uterus based on sensor signals (e.g., orientation sensor signals), and identifying an aortocaval compression condition based on such orientation metric(s) alone or in combination with other input data (e.g., other sensor-based data, non-sensor-based data, historical data, etc.).

For example, in one example embodiment, system 10 identifies an aortocaval compression condition only when the upright tilt angle is lower than a defined threshold value. Thus, if the user is in an upright position, system 10 does not identify an aortocaval compression condition, regardless of the detected lateral tilt angle. However, when the upright tilt angle decreases below a defined upright tilt angle threshold, system 10 may identify an aortocaval compression condition when the detected lateral tilt angle meets some defined threshold criteria (e.g., threshold tilt angle and duration).

In some embodiments, system 10 dynamically adjusts the upright tilt angle threshold based on the stage of pregnancy (which may be manually entered into system 10 or automatically determined/estimated by system 10 based on sensor signals) and/or other parameter(s). In other embodiments, system 10 may dynamically adjust the upright tilt angle threshold as a function of the detected lateral tilt angle, or vice versa. For example, for a lateral tilt angle of 0 degrees (user lying completely flat or supine), system 10 may apply an upright tilt angle threshold of 60 degrees. However, for a lateral tilt angle of 10 degrees, system 10 may adjust the upright tilt angle threshold to 30 degrees, such that the system will not generate an alert until the detected upright tilt angle drops below 30 degrees. In such a fashion, repositioning alerts can be provided based on combinations of lateral tilt angles and upright tilt angles, so as to only provide alerts when the probability of aortocaval compression is sufficiently high.

As discussed herein, aortocaval compression causes characteristic biometric changes. For example, when the inferior vena cava is sufficiently compressed by the gravid uterus, venous return to the heart may decrease. This decrease in cardiac preload (end diastolic ventricular pressure) can ultimately cause a reduction in cardiac output and blood pressure. This may result in a reflexive increase in systemic vascular resistance, or heart rate, or both, in an attempt to compensate for the drop in cardiac output. However, depending on the degree of aortocaval compression, there may not be any overt changes in vital signs. As described herein, aortocaval compression can cause characteristic changes in heart rate variability (HRV) that may occur before there are any overt changes in heart rate (HR), such that changes in HRV may provide an early indicator of a physiologic derangement. Thus, some embodiments of system 10 are configured to monitor the user's HR and HRV, and detect changes in HRV that are characteristic of aortocaval compression.

Maternal and Fetal Heart Rate and Heart Rate Variability

System 10 may analyze heart rate variability (HRV) using any suitable algorithms or techniques, including analyzing the R-R interval signal power spectral density (PSD), use of fractal dimensions, or discrete wavelet transformations, or any other algorithms or techniques known in the art. For example, some techniques for analyzing heart rate variability are described in (1) "Heart rate variability: Standards of measurement, physiological interpretation, and clinical use," *European Heart Journal* (1996) 17, 354-381; (2) Joseph E. Mietus and Ary L. Goldberger, M.D., "Heart Rate Variability Analysis with the HRV Toolkit," https://physionet.org/tutorials/hrv-toolkit/; and (3) Kenneth C. Bilchick; and Ronald D. Berger, "Heart Rate Variabilit," *Journal of Cardiovascular Electrophysiology,* 2006; 17(6):691-694, the contents of which articles are hereby incorporated by reference.

In one embodiment, system 10 is configured to analyze HRV by determining the power spectra across a series of R-R intervals using a fast Fourier transformation. System 10 may divide the power spectrum into low frequency bands (0.04-0.15 Hz) and high frequency bands (0.15-0.4 Hz). System 10 may use the normalized high-frequency power spectra (high-frequency power/total power) as an index of vagal activity modulation, and conversely use the normalized low frequency power (low-frequency power/total power) as an index of sympathetic activity modulation. System 10 may use the low/high frequency power ratio as an index of sympathovagal balance. In pregnant women, it has been shown that the low/high frequency power ratio is typically highest in the supine position, followed by the right lateral decubitus position, followed by the left lateral decubitus position. Thus, system 10 may be configured to use the low/high frequency power ratio as input (e.g., combined with a detected orientation and/or other biometric parameters) for identifying an aortocaval compression condition.

In addition (or alternatively) to monitoring maternal biometric parameters, system 10 may be configured to monitor and analyze one or more fetal biometric parameters that may provide valuable information regarding the health or status of the fetus. For example, the fetal heart rate pattern may provide an early indication of a compromised fetal state. For example, it has been determined that the fetal heart rate, particularly at late gestation, fluctuates in a characteristic manner, and that certain characteristic patterns in fetal heart rate variability are strongly associated with fetal acidosis and fetal hypoxia, such as a persistently minimal or absent variation in the fetal heart rate. Some embodiments of system 10 are configured to extract the fetal EKG from a maternal EKG signal generated by appropriate sensor(s) 14, using extraction methods well known in the art, including nonlinear techniques such as state space projections and frequency tracking, for example. For example, some techniques for extracting and analyzing fetal HR and HRV from the mother's EKG signal are described in (1) Khaldon Lweesy, Luray Fraiwan, Christoph Maier, and Hartmut Dickhaus, "Extraction of fetal heart rate and fetal heart rate variability from mother's ECG signal," *International Journal of Medical, Health, Biomedical, Bioengineering and Pharmaceutical Engineering*, Vol. 3, No. 6, 2006; and (2)

Gizeaddis Lamesgin, Yonas Kassaw, and Dawit Assefa, "Extraction of Fetal ECG from Abdominal ECG and Heart Rate Variability Analysis," *Afro-European Conference for Industrial Advancement*, Vol. 334 of the series *Advances in Intelligent Systems and Computing*, pp. 65-76, the contents of which articles are hereby incorporated by reference.

Some extraction methods leverage Fourier's theorem, which states that a periodic function that is reasonably continuous (such as the maternal and fetal EKG) may be expressed as a weighted sum of sinusoidal components, each of which has specific amplitude and phase coefficients. Given that the fetal EKG has a faster heart rate and lower amplitude than the maternal EKG, the underlying fetal heart rate can be extracted by system 10 executing appropriate algorithm(s).

In addition or alternatively to HRV, some embodiments of system 10 are configured to monitor one or more other biometric parameters that may indicate acute changes in a user's cardiovascular physiology, such as galvanic skin response, heat flux, and skin temperature, for example. System 10 may be configured to analyze multiple biometric parameters independently, or in combination, to identify an aortocaval compression condition.

As discussed in detail herein, knowing the orientation and location of sensor attachment with respect to the user is important. In some embodiments, the orientation and location of the sensor can automatically be determined by analyzing biometric data. In some embodiments, the device contains a bioimpedance sensor or EKG electrodes. Electrical potentials generated by the heart propagate through tissues in a characteristic fashion. By analyzing the heart's depolarization and repolarization waves in a plurality of vectors from skin surface electrodes, the relative location and orientation of the sensor with respect to the heart can be determined. In other embodiments, one or more accelerometers can be used to monitor rhythmic biomechanical activity, such as breathing and pulse. These rhythmic biomechanical processes create characteristic accelerometric distortions that can be measured from the surface of the body. A profile of the expected accelerometric changes that occur at each location of the body can be provided, and thus the sensor can automatically determine its location with respect to the body based on measured biomechanical activity.

Alerts

In some embodiments, system 10 is configured to generate an alert, e.g., a repositioning alert, to a user upon identifying an aortocaval compression condition or upon a detection that selected biometric parameter(s) exceed corresponding threshold value(s). For example, system 10 may generate a repositioning alert upon detecting an acute change in maternal or fetal heart rate (or heart rate variability). In some embodiments, system 10 generates alerts in response to defined biometric parameters only if the user meets certain position or activity parameters. For example, if the user is upright, acute changes in biometric parameters may not trigger repositioning alerts. When the system 10 determines that the aortocaval compression condition is no longer present (e.g., for a particular consecutive duration of time), e.g., due to the user repositioning herself in response to the alert, system 10 may turn off the alert and continue monitoring for a next aortocaval compression condition.

In some embodiments, if system 10 detects that the user is sufficiently active, subsequent changes in biometric parameters may not trigger repositioning alerts. This may occur in situations where the user is exercising and heart rate changes are expected to occur in the absence of aortocaval compression. In one embodiment, if a user is below a threshold upright tilt angle and/or sufficiently inactive, repositioning alerts can be provided based on changes in biometric parameters or lateral tilt angle, or a combination of both. Conversely, system 10 may suspend repositioning alerts if a user is above a threshold upright tilt angle and/or sufficiently active.

In some embodiments, system 10 uses both a left lateral tilt angle threshold and a right lateral tilt angle threshold for identifying an aortocaval compression condition, wherein system 10 may set and/or adjust the left and right lateral tilt angle thresholds independently of each other. Based on the anatomic location of the inferior vena cava, which is more susceptible to vascular compression than the aorta, left lateral tilt positions may be preferred over right lateral tilt positions, with respect to avoiding aortocaval compression. For example, a pregnant woman may not experience any significant vascular compression at left lateral tilt angles of above 15 degrees, but may experience vascular compression at right lateral tilt angles of up to 30 degrees. Therefore, in some embodiments, system 10 may utilize a right lateral tilt angle threshold that is higher than a corresponding left lateral tilt angle threshold. Further, system 10 may apply different algorithms or look-up tables for adjusting the left and right lateral tilt angle thresholds as a function of other biometric parameter(s). For example, such algorithms or look-up tables may implement a different sensitivity to changes in biometric parameters for the two different lateral tilt angles. Thus, for instance, given that inferior vena cava compression is more likely to occur in the right lateral tilt position than in the left lateral tilt position, system 10 may be configured (via the relevant algorithms or look-up tables implemented by system 10) to identify an aortocaval compression condition and trigger an alert in response to more subtle changes in biometric parameters when a user is in the right lateral tilt position as opposed to left lateral tilt position.

Some embodiments of system 10 incorporate information regarding maternal anatomy (e.g., BMI), the stage of the pregnancy, and/or the health condition of the fetus (e.g., intrauterine growth restriction or fetal macrosomia) as input for identifying an aortocaval compression condition. It is known that the probability for aortocaval compression is related to maternal anatomy and gestational age, thus system 10 may automatically adjust thresholds for identifying an aortocaval compression condition and generating alerts based on such information. For example, at the earliest stages of pregnancy, when the uterus is small and less likely to cause aortocaval compression, system 10 may apply less stringent orientation and duration thresholds for identifying an aortocaval compression condition (e.g., system 10 may allow more time in a supine position before triggering an alert or require more lateral tilt before considering the user as non-supine). However, as the gestational age increases, so does the probability for aortocaval compression. Thus, system 10 may automatically adjust the orientation and duration thresholds required to identify an aortocaval compression condition and trigger and alert based gestational age. System 10 may automatically adjust the orientation and duration thresholds (in an increasingly restrictive direction) as the gestational age increases. Further, it has been shown that in pregnancies complicated by intrauterine growth restriction, the fetus may be particularly susceptible to the deleterious effects of even minor levels of aortocaval compression. Thus, in such instances, system 10 may adjust the relevant thresholds to help avoid even minor levels of aortocaval compression.

As discussed above, some embodiments utilize maternal and/or fetal heart rate (HR) and/or heart rate variability (HRV) as input for identify an aortocaval compression condition. Maternal and/or fetal HR and HRV can serve as valuable early indicators of aortocaval compression, even in positions that would otherwise not suggest an aortocaval compression condition. As discussed above, the specific lateral tilt angles that can cause aortocaval compression are typically dependent on maternal anatomy, gestational age, and other factors. In some embodiments, system 10 is configured to learn relationships between maternal position and particular markers of aortocaval compression (e.g., maternal and/or fetal HR or HRV changes) over time and automatically adjust relevant thresholds accordingly. For example, if system 10 detects significant maternal or fetal heart rate changes (e.g., HR or HRV above some threshold value(s)) every time a particular user assumes a supine position for more than 10 minutes, system 10 may adjust one or more relevant alert thresholds such that system 10 alerts the user before such biometric changes are anticipated. Incorporating such vital signs and/or biometric data in addition to the detected orientation data may reduce the rate of false negative and false positive alerts. Furthermore, system 10 may provide increased safety and personalized position recommendations by incorporating learning algorithms that automatically adjust alert thresholds and/or parameters based on identified historical relationships specific to the particular user (e.g., relationships between maternal position and maternal/fetal biometric data).

Example Algorithms for Monitoring for an Aortocaval Compression Condition

Figure 4:
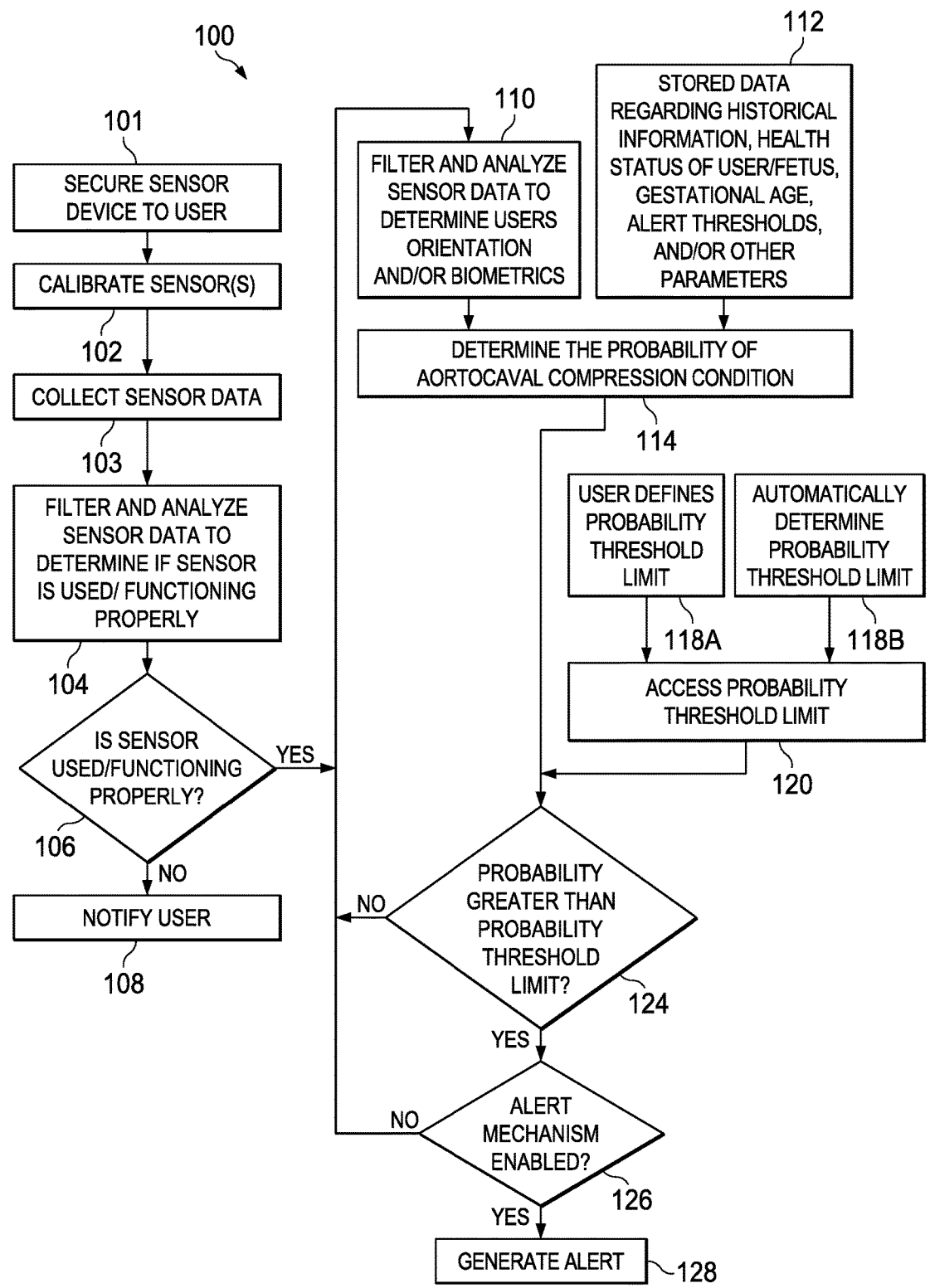
FIG. 4 illustrates an example algorithm for monitoring for the presence of aortocaval compression and generating an alert, according to one embodiment.

FIG. 4 illustrates an example algorithm 100 for monitoring for an aortocaval compression condition and generating an alert, according to one embodiment. Algorithm 100 may be implemented by system 100, e.g., stored in storage unit 20 and executed by processing unit 18.

At 101, a sensor device including sensor(s) 14 is secured directly or indirectly to a user (pregnant woman), e.g., proximate the umbilical. At 102, a sensor calibration process may be performed. In one embodiment, the user orients herself in a specified position, e.g., standing upright or lying supine with no upright or lateral tilt. Once in the specified position, the user may press a button or otherwise provide input to system 10 to initiate a calibration. System 10 may then calibrate each sensor 14 (e.g., one or more accelerometers) by resetting all sensor angles to zero or other predefined angle (e.g., 90, 180, etc.). Such calibration may be operable, e.g., to compensate for discrepancies in between the orientation of the sensor device secured to the user and the orientation of the user herself (or the uterus). For example, the calibration process may correct for non-zero tilt angles (e.g., upright and/or lateral tilt angles) of the sensor when the user is lying in a supine, non-tilted position, in which zero tilt angles of the sensor device may be expected. In some embodiments, the user is informed how to perform the calibration process by instructions written on the sensor device or included in the packaging of system 10. In other embodiments, system 10 may be configured to guide the user through the calibration process in real-time, e.g., using recorded verbal instructions or other audible feedback.

At 103, sensor(s) 14 may begin generating sensor signals associated with one or more parameters of the user or fetus, e.g., orientation sensor data (e.g., accelerometer signals) useful for determining user orientation, and/or other sensor data useful for determining one or more biometric or other parameters of the user or fetus, e.g., any of the various parameters discussed above. Sensor signals generated by sensor(s) 14 may also be referred to as sensor data. Sensor(s) 14 may communicate the sensor data to processing unit 18 for processing.

At 104, processing unit 18 may filter and analyze the sensor data to determine whether the sensor(s) 14 is/are applied and functioning properly. Processing unit 18 may apply any suitable data filters (e.g., low-pass and/or high-pass filters) to the sensor data, and may compare the filtered sensor data to one or more thresholds, e.g., signals or values corresponding to a typical range of signals or values historically observed during proper application and functioning of the respective type(s) of sensor(s) 14, and identify a sensor error (e.g., due to the sensor being improperly applied to the user or being defective) if the received sensor data exceeds a defined threshold or falls outside a defined range of signals/values corresponding to proper sensor functioning. According to decision step 106, if a sensor error is detected, processing unit 18 may generate a notification and output the notification to the user via a display device 26 and/or alert mechanism 30, as indicated at 108. If no sensor error is detected, the method may proceed to step 110.

At 110, processing unit 18 may further filter and analyze the sensor data to determine an orientation of the user and/or one or more biometric parameters of the user (e.g., heart rate, heart rate variability, activity level, etc.). In some embodiments, determining the orientation of the user may include determining orientation metrics including an upright tilt angle, a lateral tilt angle, or both from the sensor data.

At 112, processing unit 18 may access relevant data from storage unit 20, e.g., historical sensor-based or non-sensor-based data regarding the user and/or fetus, health status information regarding the user and/or fetus, gestational age, alert thresholds, and/or any other data relevant for identifying an aortocaval compression condition.

At 114, processing unit 18 may determine a probability of an aortocaval compression condition based on the determined user orientation metrics and/or biometric parameter(s) determined at 110 and the stored data accessed at 112. Processing unit 18 may utilize any algorithm(s) and/or look-up tables to determine the probability of aortocaval compression condition based on such input data. For example, processing unit 18 may utilize an equation that receives, as inputs, an upright tilt angle and lateral tilt angle determined at 110 and a health status of the user and gestational age accessed at 112, and outputs a probability of aortocaval compression condition.

In parallel, system 10 may determine a probability threshold at 118A or 118B. At 118A, a probability threshold may be selected by the user or other person (e.g., caregiver), e.g., by direct user selection of a probability limit, or indirectly by user selection of a setting having an associated probability threshold known by processing unit 18 (e.g., a user may select from low, medium, or high detection sensitivity, which correspond to predefined probability thresholds of 90%, 70%, and 50%, respectively). Alternatively, at 118B, system 10 may automatically determine or select a probability threshold for the user, e.g., based on particular sensor data, historical data, user-input data, or other input.

At 120, processing unit 18 may access the probability threshold selected or determined at 118A or 118B. At 124, processing unit 18 may then compare the probability of an aortocaval compression condition determined at 114 with the probability threshold accessed at 120 to determine whether to generate an alert. If the determined probability does not exceed the probability threshold, the method may return to 110 to analyze further sensor data (e.g., for a subsequent time period).

However, if the determined probability exceeds the probability threshold, processing unit 18 may then determine whether an alert mechanism 30 is enabled at 126, and if so, generate an alert to the user at 128 (e.g., a tactile, auditory, and/or visual alert) via a display device 26 and/or alert mechanism 30.

Figure 5:
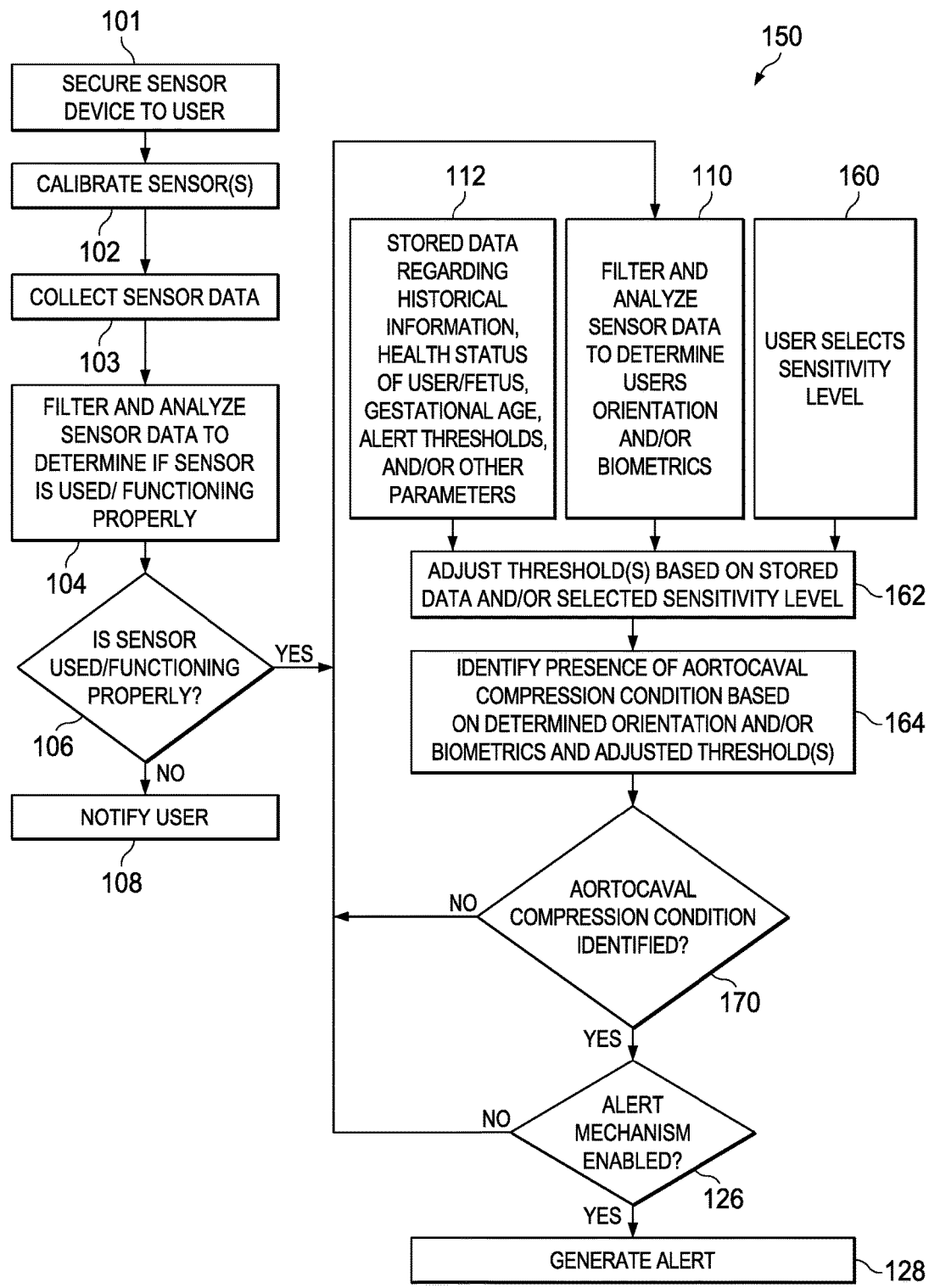
FIG. 5 illustrates another example algorithm for monitoring for the presence of aortocaval compression and generating an alert, according to one embodiment.

FIG. 5 illustrates another example algorithm 150 for monitoring for an aortocaval compression condition and generating an alert, according to one embodiment. Algorithm 150 may be implemented by system 100, e.g., stored in storage unit 20 and executed by processing unit 18. Algorithm 150 is generally similar to algorithm 100 shown in FIG. 4, but includes the concept of adjusting one or more threshold values based on a user-selected sensitivity setting, and determines the presence (or not) of an aortocaval compression condition without explicitly calculating a probability of an aortocaval compression condition.

Thus, as shown, algorithm 150 includes steps 101-112 and 126-128 of algorithm 100 shown in FIG. 4, and further includes steps 160-170 that differ from steps 114-124 of algorithm 100.

Thus, a sensor device including sensor(s) 14 is secured to a user at 101, a sensor calibration process may be performed at 102, and sensor(s) may begin generating sensor data at 103. The sensor data may be filtered and analyzed at 104 to identify sensor errors. If a sensor error is detected at decision step 106, processing unit 18 may generate a notification at 108; alternatively, if no sensor error is detected, the algorithm proceeds to step 110.

At 110, processing unit 18 may further filter and analyze the sensor data to determine an orientation of the user (e.g., an upright tilt angle and/or lateral tilt angle) and/or one or more biometric parameters of the user (e.g., heart rate, heart rate variability, activity level, etc.). At 112, processing unit 18 may access relevant data from storage unit 20, e.g., historical sensor-based or non-sensor-based data regarding the user and/or fetus, health status information regarding the user and/or fetus, gestational age, alert thresholds, and/or any other data relevant for identifying an aortocaval compression condition.

At 160, the user (or other person, e.g., a caregiver) may select a sensitivity level for system 10, e.g., via a user interface 40 (e.g., button(s) or touchscreen) on the sensor device, or via a user interface provided by an application residing on or accessible at a computer (e.g., laptop, tablet, smartphone, etc.) communicatively linked to the sensor device (e.g., via wireless connection). The user-selected sensitivity level generally defines the sensitivity of aortocaval compression detections (and thus alerts) by system 10; the higher the sensitivity level, the more likely system 10 will determine an aortocaval compression condition and thus generate an alarm in a given situation. In some embodiments, the user interface may allow the user to select from a discrete number of sensitivity levels, e.g., high sensitivity, medium sensitivity, or low sensitivity.

At 162, processing unit 18 may set or adjust one or more threshold value(s) (used for identifying the presence (or not) of an aortocaval compression condition at step 164) based on (a) the user-selected sensitivity level, (b) particular stored data accessed at 112, and/or (c) particular sensor-based parameter(s) determined at 110, using any suitable algorithms, look-up tables, etc.

With respect to the user-selected sensitivity level, each different sensitivity level may be assigned a respective value for a particular threshold. For instance, for a left-side lateral tilt angle threshold, a "high" sensitivity level may be assigned a threshold value of 20 degrees, a "medium" sensitivity level may be assigned a threshold value of 15 degrees, and a "low" sensitivity level may be assigned a threshold value of 10 degrees, wherein the processing unit 18 applies the threshold value corresponding to the selected sensitivity level. As another example, each different sensitivity level may be assigned a weight or multiplier for a particular threshold, which may be applied to a default or baseline threshold value, or threshold value determined based on other inputs. For instance, for a left-side lateral tilt angle threshold, a "high" sensitivity level may be assigned a multiplier of 1.0, a "medium" sensitivity level may be assigned a multiplier of 0.85, and a "low" sensitivity level may be assigned a multiplier of 0.65, wherein the processing unit 18 applies the multiplier to an example default or baseline value of 20 degrees for the left-side lateral tilt angle threshold. In some embodiments, multiplier(s) based on other factors (e.g., particular stored data accessed at 112 and/or particular sensor-based parameter(s) determined at 110) may be further multiplied to the default or baseline threshold value.

As mentioned above, processing unit 18 may also set or adjust particular threshold value(s) based on particular stored data accessed at 112, and/or particular sensor-based parameter(s) determined at 110. For example, different values or value ranges of a particular stored data item (e.g., gestational age) or particular sensor-based parameter (e.g., user activity level) may be assigned a respective value, weight or multiplier for a particular threshold, e.g., as discussed above with respect to the user-selected sensitivity level. As another example, processing unit 18 may set or adjust a particular threshold value as a mathematical function of the value of the particular stored data item (e.g., gestational age) or sensor-based parameter (e.g., user activity level). For example, processing unit 18 may automatically adjust the left-side lateral tilt angle threshold value on a daily basis by applying the following multiplier to the threshold value:

(1000 days−gestational age (days))/1000 days

As another example, processing unit 18 may automatically and dynamically adjust a heart rate variability threshold value ($HRV_{limit}$) every minute as a function of a detected activity level value (A) by applying a multiplier of C*A to a baseline value for $HRV_{limit}$ (wherein C is a constant), or according to the equation:

$$HRV_{limit\_adjusted} = (HRV_{limit\_baseline})^{C*A}$$

It should be understood that the examples presented above are provided only to illustrate some example relationships between various types of (sensor-based and non-sensor-based) parameters and particular threshold values utilized by processing unit 18.

The threshold or threshold value for any particular parameter being analyzed (e.g., an orientation metric or biometric parameter) may include multiple components, e.g., magnitude component and a duration component. For example, the upright tilt angle threshold value may include a magnitude component of 40 degrees and a duration component of 10 minutes, such that the upright tilt angle threshold value is only exceeded when the user maintains an upright tilt angle of less than 40 degrees for a consecutive period of at least 10 minutes. Thus, for such magnitude/duration type threshold values, system 10 may be configured to set or adjust one or both component values, i.e., the magnitude value, duration value, or both. For example, referring to the example above in which a left-side lateral tilt angle threshold value is automatically adjusted by a multiplier based on gestational age, and assuming left-side lateral tilt angle threshold value has a minimum angle component and a minimum duration component, system 10 may apply the gestational-age-based multiplier to the minimum angle component, or to the minimum duration component, or to both components of the threshold, depending on the particular embodiment or system setting.

At 164, processing unit 18 may identify the presence of an aortocaval compression condition based on the orientation metric(s) and/or biometric parameter(s) determined at 110 and one or more corresponding threshold values, which may include any threshold value(s) adjusted at 162, using any suitable algorithm(s), rule(s), look-up table(s), or other techniques. For example, processing unit 18 may independently compare each orientation metric and each biometric parameter (if any) with a corresponding threshold value, and identify an aortocaval compression condition only if each orientation metric and biometric parameter (if any) exceeds its corresponding threshold value. An example of such embodiment is discussed below with respect to algorithm 200 shown in FIG. 7.

As another example, processing unit 18 may independently compare each orientation metric and each biometric parameter (if any) with a corresponding threshold value, and identify an aortocaval compression condition only if any one, or a defined minimum number (e.g., 2 or 3) of the orientation metrics or biometric parameters (if any) exceeds its corresponding threshold value.

As another example, processing unit 18 may mathematically combine two or more orientation metrics and/or biometric parameters to calculate a multi-parameter score, compare the multi-parameter score to a corresponding threshold value, and identify an aortocaval compression condition if the multi-parameter score exceeds the threshold value.

As used herein, a value may "exceed" a threshold value if the value is greater than a maximum limit threshold or less than a maximum limit threshold.

Referring to decision step 170, if an aortocaval compression condition is not identified at 164, the method may return to 110 to analyze and evaluate a next set of sensor data (e.g., corresponding to sensor data collected during a subsequent time period). However, if an aortocaval compression condition is identified, processing unit 18 may then determine whether an alert mechanism 30 is enabled at 126, and if so, generate an alert to the user at 128 (e.g., a tactile, auditory, and/or visual alert) via a display device 26 and/or alert mechanism 30.

Figure 6:
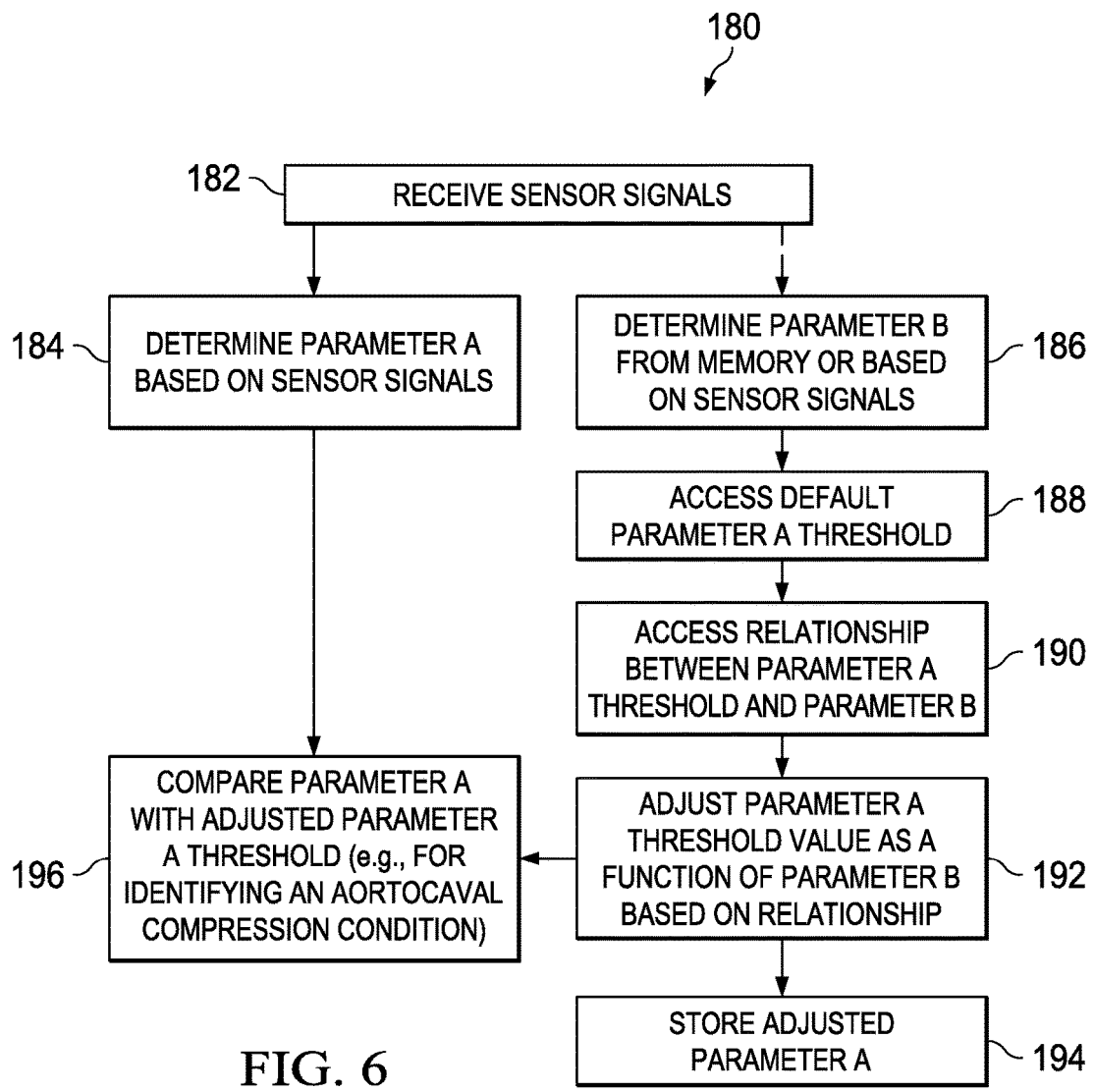
FIG. 6 illustrates an example algorithm for dynamically adjusting a threshold value for a first sensor-based parameter based on the value of a different sensor-based or non-sensor-based parameter, according to one embodiment.

FIG. 6 illustrates an example algorithm 180 for dynamically adjusting a threshold value for a first sensor-based parameter (parameter A) based on the value of a different sensor-based or non-sensor-based parameter (parameter B), according to one embodiment. Algorithm 180 may be implemented by system 100, e.g., stored in storage unit 20 and executed by processing unit 18.

At 182, processing unit 18 may receive sensor signals from one or more sensors 14 of system 10. At 184, processing unit 18 may determine a parameter A, e.g., lateral tilt angle, heart rate variability, activity level, etc. based on received sensor signals. At 186, processing unit 18 may determine another parameter B, e.g., a sensor-based parameter determined based on the received sensor signals, or a non-sensor-based parameter accessed from storage 20.

At 186, processing unit 18 may access a default or baseline threshold value for parameter A, e.g., a lateral tilt angle of 15 degrees. At 190, processing unit 18 may access a stored relationship between the parameter A threshold value and parameter B, e.g., embodied as an equation or look-up table. For example, the stored relationship may comprise the following relationship between a sensor-based lateral tilt angle threshold value (parameter A threshold value) and a sensor-based upright tilt angle (parameter B):

$$\text{threshold}_{lateral\_tilt\_adjusted} = \text{threshold}_{lateral\_tilt\_baseline} * (1 - \text{upright tilt angle}/30)$$

At 192, processing unit 18 may adjust the parameter A threshold value based on the accessed relationship and the value of parameter B, and store the adjusted parameter A threshold value in storage unit 20 at 194. At 196, processing unit 18 may then compare the value of parameter A determined at 184 with the adjusted parameter A threshold value, e.g., as part of an algorithm for identifying the presence of an aortocaval compression condition (e.g., at step 164 of algorithm 150 shown in FIG. 5).

Figure 7:
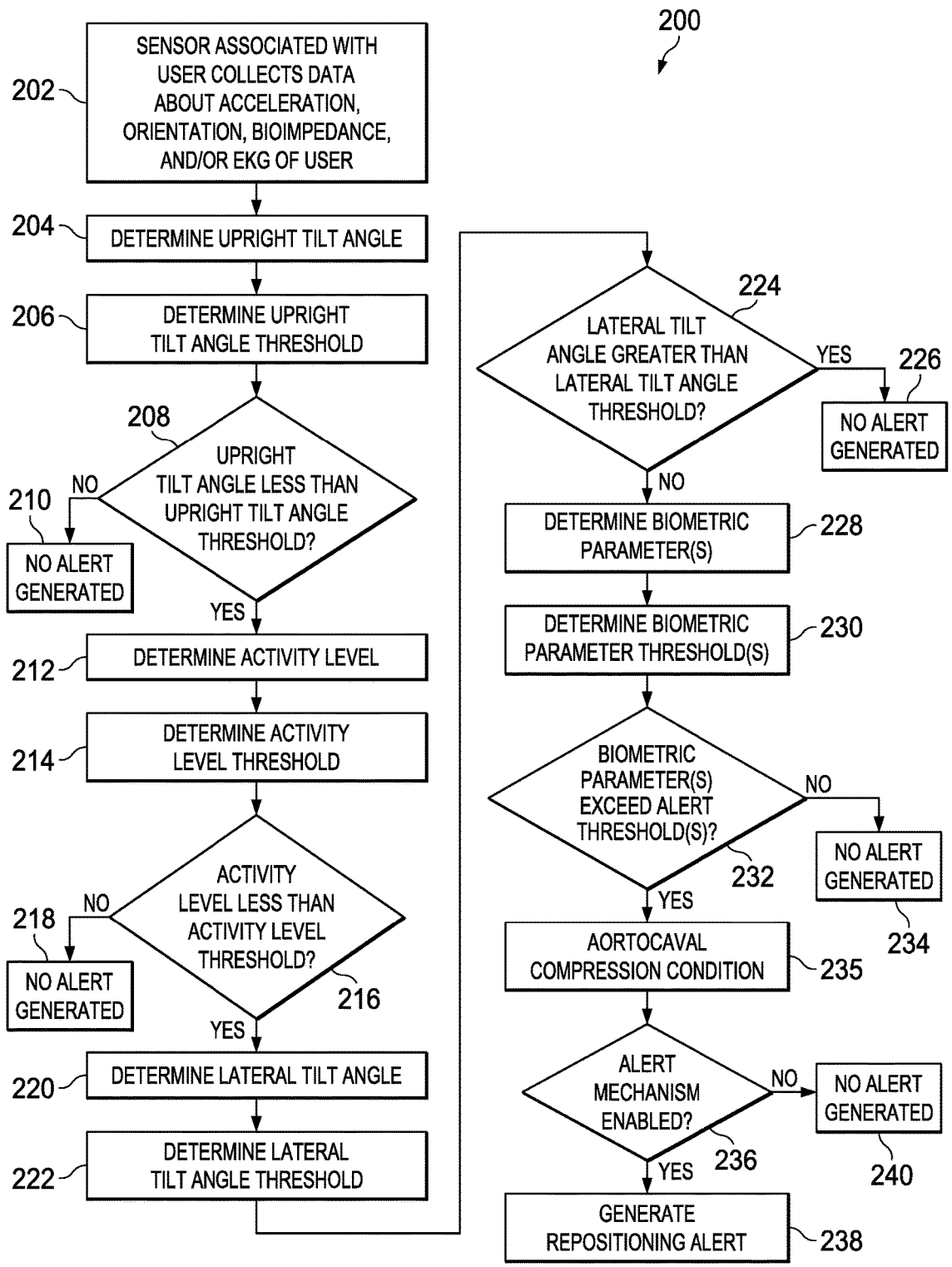
FIG. 7 illustrates another example algorithm for monitoring for an aortocaval compression condition and generating an alert, according to one embodiment.

FIG. 7 illustrates another example algorithm 200 for monitoring for an aortocaval compression condition and generating an alert, according to one embodiment. Algorithm 200 may be implemented by system 100, e.g., stored in storage unit 20 and executed by processing unit 18. In general, algorithm 200 independently compare each of a number of parameters to a respective threshold value, and identifies an aortocaval compression condition only if each parameter exceeds its corresponding threshold value.

At 202, a sensor device including sensor(s) 14 is secured directly or indirectly to a user (pregnant woman), e.g., proximate the umbilicus, and begins generating sensor signals associated with one or more parameters of the user or fetus, e.g., accelerometer data, bioimpedance sensor data, and or EKG signals, for example. Step 202 may also include a sensor calibration process, e.g., as discussed above at step 102 of algorithm 100. Sensor(s) 14 may communicate the sensor data to processing unit 18 for processing.

At 204, processing unit 18 may determine an upright tilt angle based on the accelerometer data. At 206, processing unit 18 may access or determine an upright tilt angle threshold, according to any techniques discussed herein (e.g., including suitable adjustments to the threshold). At 208, processing unit 18 may compare the determined upright tilt angle to the upright tilt angle threshold. If the determined upright tilt angle is greater than or equal to the upright tilt angle threshold, no alert is generated, as indicated as 210. Alternatively, if the determined upright tilt angle is less than the upright tilt angle threshold, the algorithm proceeds to 212.

At 212, processing unit 18 may determine an activity level of the user, e.g., based on the accelerometer data. For example, processing unit 18 may identify steps based on defined acceleration impulses that correspond with steps (e.g., particular sudden accelerations), and maintain a count of steps over time to calculate an activity level metric based on the step count over time. As another example, processing unit 18 may identify and count all major body movements, including steps and other movements such as sitting down, lying down, sitting up from a lying position, standing up from a sitting position, rolling over, etc., and calculate an activity level metric based on the type and/or count of such movements over time. For example, processing unit 18 may employ an algorithm similar to the algorithms employed in any of the various activity tracking devices currently on the market.

At 214, processing unit 18 may access or determine an activity level threshold, according to any techniques discussed herein (e.g., including suitable adjustments to the threshold). At 216, processing unit 18 may compare the determined activity level metric to the activity level threshold. If the determined activity level metric is less than or equal to the activity level threshold, no alert is generated, as indicated as 218. Alternatively, if the determined activity level metric is greater than the activity level threshold, the algorithm proceeds to 220.

At 220, processing unit 18 may determine a lateral tilt angle based on the accelerometer data. At 222, processing unit 18 may access or determine a lateral tilt angle threshold, according to any techniques discussed herein (e.g., including suitable adjustments to the threshold). At 224, processing unit 18 may compare the determined lateral tilt angle to the lateral tilt angle threshold. If the determined lateral tilt angle is greater than or equal to the lateral tilt angle threshold, no alert is generated, as indicated as 226. Alternatively, if the determined lateral tilt angle is less than the lateral tilt angle threshold, the algorithm proceeds to 228.

At 228, processing unit 18 may determine one or more biometric parameters of the user, e.g., based on the accelerometer signals, bioimpedance signals, and/or EKG or EKG signals collected at 202. For example, processing unit 18 may determine a heart rate and/or heart rate variability of the user and/or the fetus, a breathing rate of the user, and/or other biometric parameter(s).

At 230, processing unit 18 may access or determine a biometric parameter threshold corresponding to each biometric parameter determined at 228, according to any techniques discussed herein (e.g., including suitable adjustments to the threshold). At 232, processing unit 18 may compare each determined biometric parameter to its respective biometric parameter threshold. For an embodiment in which only one biometric parameter is analyzed at steps 228-232, if the determined biometric parameter exceeds the corresponding biometric parameter threshold, an aortocaval compression condition is identified, as indicated at 235. Processing unit 18 may then determine whether an alert mechanism 30 is enabled at 236, and if so, generate and output a repositioning alert to the user at 239 via a display device 26 and/or alert mechanism 30. Alternatively, if it is determined at 232 that the determined biometric parameter does not exceed the corresponding biometric parameter threshold, no alert is generated, as indicated at 234.

For embodiments in which multiple biometric parameters are analyzed at steps 228-232, in some embodiments an aortocaval compression condition may be identified (235) only when each biometric parameter exceeds its respective biometric parameter threshold, while in other embodiments an aortocaval compression condition may be identified (235) when one or some predefined number (e.g., two or three) of the biometric parameters exceed their respective biometric parameter thresholds.

Figure 8:
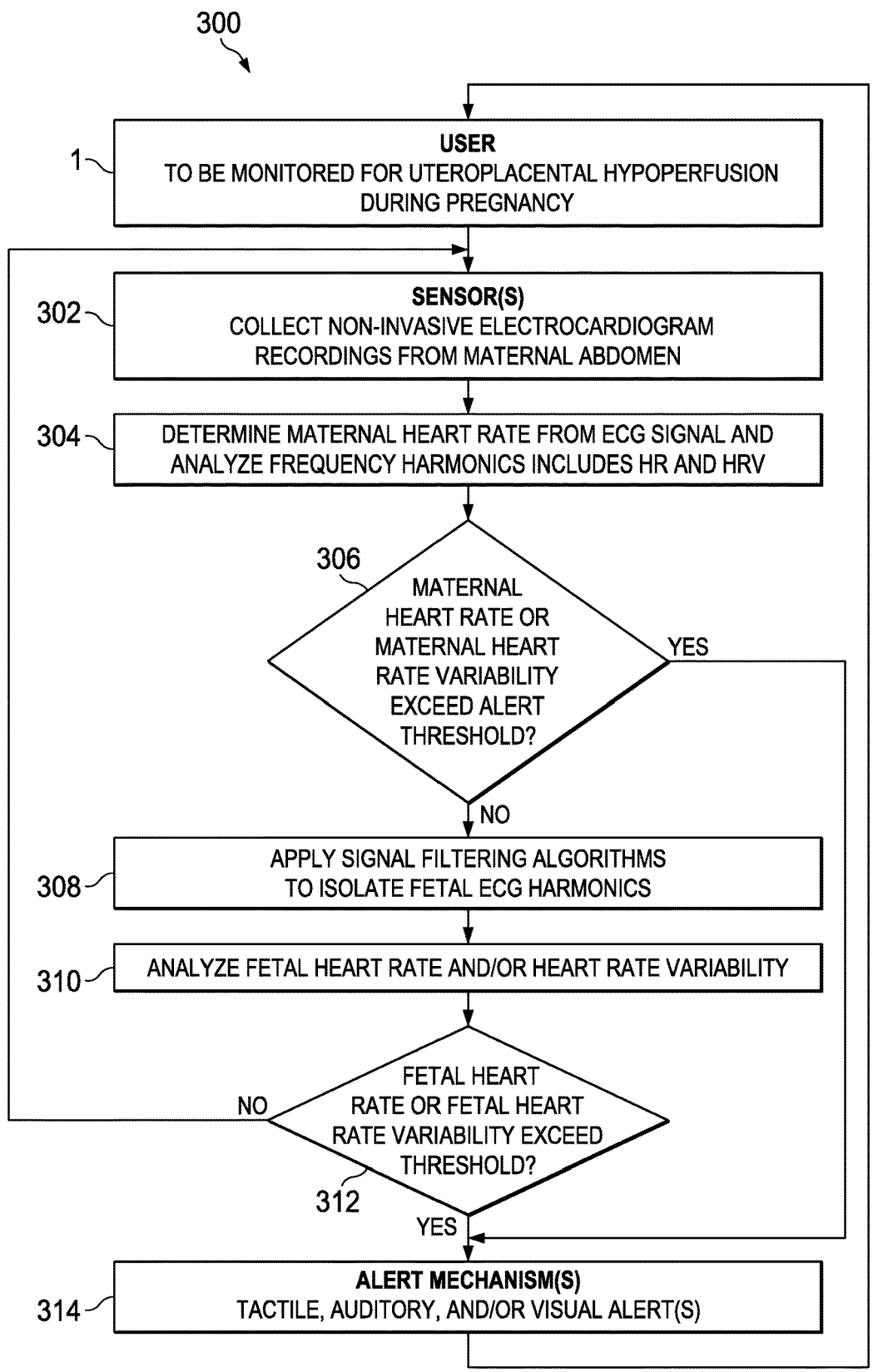
FIG. 8 illustrates an example algorithm for detecting and evaluating both the maternal heart rate and fetal heart rate and monitoring for an aortocaval compression condition based on such evaluations, according to one embodiment.

FIG. 8 illustrates an example algorithm 300 for detecting and evaluating both the maternal heart rate and fetal heart rate and monitoring for an aortocaval compression condition based on such evaluations, according to one embodiment. In this example embodiment, algorithm 300 identifies an aortocaval compression condition if either the maternal heart rate or heart rate variability exceeds a corresponding threshold value or the fetal heart rate or heart rate variability exceeds a corresponding threshold value. Algorithm 300 may be implemented by system 100, e.g., stored in storage unit 20 and executed by processing unit 18.

As shown, a user 1 (pregnant woman) to be monitored is identified, and a sensor device including sensor(s) 14 may be secured directly or indirectly to the user 1, e.g., on the abdomen proximate the umbilical. The sensor(s) 14 may include non-invasive EKG electrodes and/or other type(s) of sensors.

At 302, EKG electrodes collect EKG recordings from the user's abdomen, and communicate the EKG signals to processing unit 18. Step 302 may also include a sensor calibration process, e.g., as discussed above at step 102 of algorithm 100. At 304, processing unit 18 may identify the maternal EKG frequency harmonics from the EKG signals, e.g., heart rate and heart rate variability, using any techniques known to one of ordinary skill in the art.

At 306, processing unit 18 may compare the maternal heart rate and/or heart rate variability with corresponding threshold value(s). If the maternal heart rate and/or heart rate variability exceeds the corresponding threshold value(s), an aortocaval compression condition is identified and an alert is generated and outputted to the user via an alert mechanism 30, as indicated at 314.

At 308, processing unit 18 may extract or isolate the fetal EKG frequency harmonics, e.g., fetal heart rate and/or heart rate variability, from the EKG signals collected at 302, using any known signal filtering algorithm(s) or techniques for extracting/isolating fetal EKG frequency harmonics, e.g., as discussed above. At 310, processing unit 18 may analyze the fetal heart rate and/or heart rate variability, and compare the fetal heart rate and/or heart rate variability with corresponding threshold value(s) at 312. If the fetal heart rate and/or heart rate variability exceed the corresponding threshold value(s), an aortocaval compression condition is identified and an alert is generated and output to the user via an alert mechanism 30, as indicated at 314.

Machine Learning Algorithms

In some embodiments, system 10 is configured to implement one or more machine learning algorithms to monitor characteristics of a particular user over time and automatically adapt one or more aspects of the algorithm(s) for identifying an aortocaval compression condition of the user, e.g., to reduce false negatives, reduce false positives, preemptively avoid aortocaval compression conditions from occurring, and/or any other manner of improving the operation of system 10. In some embodiments, system 10 implements one or more machine learning algorithms that identify and monitor patterns in one or more sensor-detected parameters of the user and/or fetus, and automatically adjusts one or more threshold values used by system 10 for identifying aortocaval compression conditions (e.g., an upright tilt angle threshold, left-side lateral tilt angle threshold, right-side lateral tilt angle threshold, heart rate threshold, heart rate variability threshold, etc.), e.g., to reduce false negatives, reduce false positives, and/or preemptively avoid aortocaval compression conditions from occurring.

Figure 9:
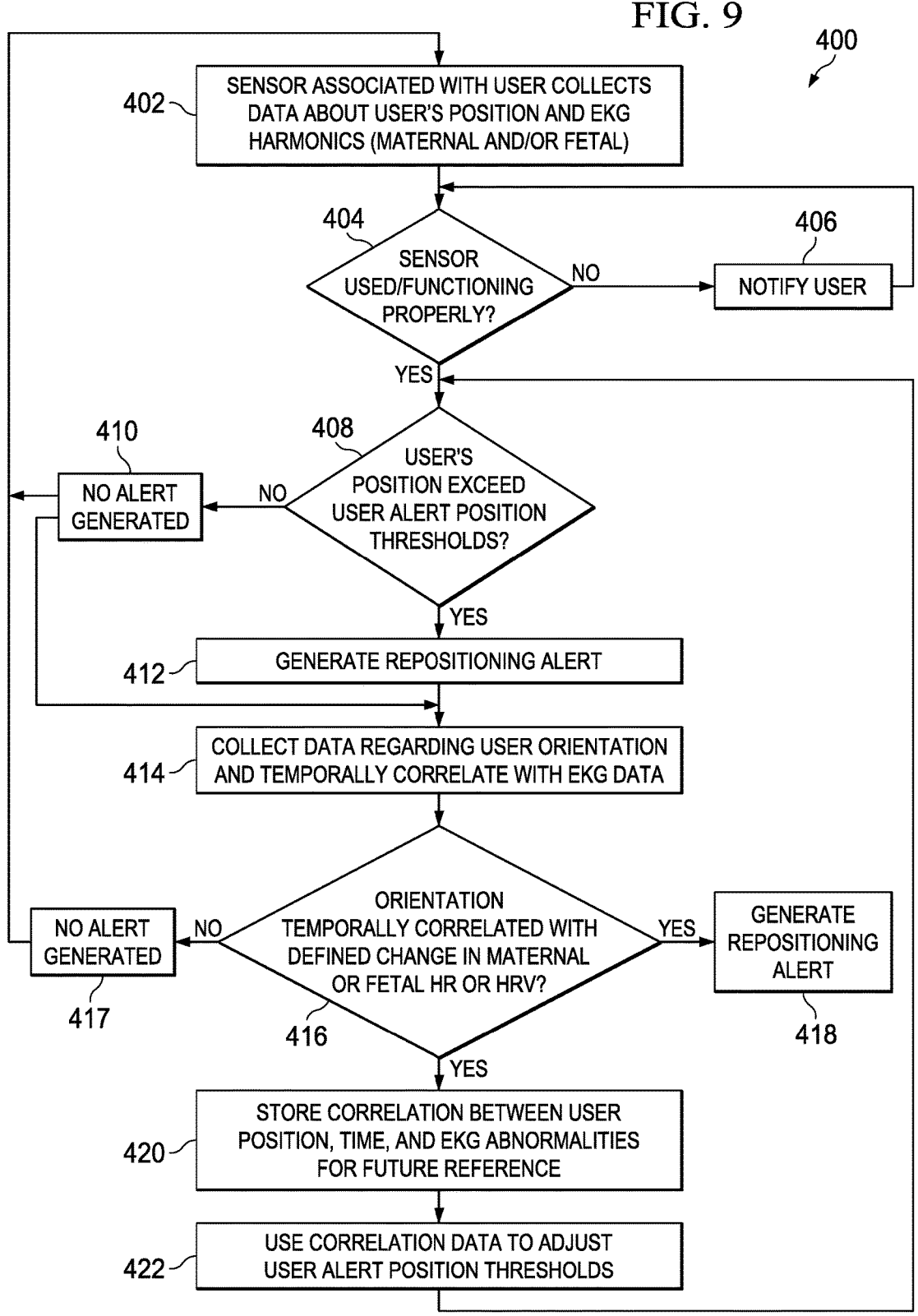
FIG. 9 illustrates an example of a machine learning algorithm for automatically adjusting threshold value(s) used for identifying an aortocaval compression condition, according to one embodiment.

FIG. 9 illustrates an example of such machine learning algorithm 400, according to one embodiment. More particularly, algorithm 400 is configured to identify an aortocaval compression condition in a user, and includes machine learning aspects for automatically adjusting one or more user orientation thresholds (e.g., upright tilt angle threshold and/or lateral tilt angle threshold(s)) based on learned information or patterns in EKG data of the user. Algorithm 400 may be implemented by system 100, e.g., stored in storage unit 20 and executed by processing unit 18.

At 402, a sensor device including sensor(s) 14 is secured directly or indirectly to a user (pregnant woman), e.g., proximate the umbilical, and begins generating sensor signals associated with one or more parameters of the user or fetus, e.g., orientation data (e.g., accelerometer data) and EKG data, for example. Step 402 may also include a sensor calibration process, e.g., as discussed above at step 102 of algorithm 100. Sensor(s) 14 may communicate the sensor data to processing unit 18 for processing.

At 404, processing unit 18 may filter and analyze the sensor data to determine whether the sensor(s) 14 is/are applied and functioning properly, e.g., as discussed above regarding step 104 of algorithm 100. If a sensor error is detected (e.g., due to improper application or a defective sensor), processing unit 18 may generate a notification and output the notification to the user via a display device 26 and/or alert mechanism 30, as indicated at 406. If no sensor error is detected, the method may proceed to step 408.

At 408, processing unit 18 may determine one or more user orientation metrics (e.g., upright tilt angle, right-side lateral tilt angle, and left-side lateral tilt angle) based on sensor signals collected at 402 during a particular time period $T_i$, and compare such user orientation metric(s) to corresponding orientation threshold value(s), e.g., as discussed in any of the algorithms discussed herein. If the user orientation metric(s) do not exceed the corresponding orientation threshold value(s) (e.g., either individually or collectively, based on the particular embodiment), no alert is generated, as indicted at 410, and the algorithm may return to 402 to collect sensor data during a next time period $T_{i+1}$. Alternatively, if the user orientation metric(s) do exceed the corresponding orientation threshold value(s) (e.g., either individually or collectively, based on the particular embodiment), an aortocaval compression condition is identified and processing unit 18 may generate an alert to the user at 412 via a display device 26 and/or alert mechanism 30.

As shown in FIG. 9, in either event (i.e., whether or not an aortocaval compression condition is identified at 408), the method may proceed to steps 414-422 for analysis of collected EKG data and/or automatic adjustment of one or more orientation threshold value(s) based on such collected EKG data.

At 414, processing unit 18 may temporally correlate the determined user orientation metrics (e.g., upright tilt angle, right-side lateral tilt angle, and left-side lateral tilt angle) corresponding with the sensor signals collected during time period $T_i$ with EKG data collected at 402 during the same time period $T_i$ (or alternatively, during a time period having a defined relationship with time period $T_i$, e.g., a subset or superset of time period $T_i$). Processing unit 18 may store such temporally correlated data in storage unit 20.

At 416, processing unit 18 may analyze the EKG data corresponding to time period $T_i$ for EKG abnormalities corresponding to an aortocaval compression condition. For example, processing unit 18 may determine one or more metrics from the EKG data, e.g., maternal heart rate, maternal heart rate variability, fetal heart rate, and/or fetal heart rate variability, and compare such EKG-based metric(s) with corresponding threshold value(s), e.g., as discussed in any of the algorithms discussed herein. If the EKG-based metric(s) do not exceed the corresponding threshold value(s) (e.g., either individually or collectively, based on the particular embodiment), no alert is generated, as indicted at 417, and the algorithm may return to 402 to collect sensor data during a next time period $T_{i+1}$.

Alternatively, if the user EKG-based metric(s) do exceed the corresponding orientation threshold value(s) (e.g., either individually or collectively, based on the particular embodiment), an aortocaval compression condition is identified and processing unit 18 may generate an alert to the user at 418 via a display device 26 and/or alert mechanism 30. In addition, at 420, processing unit 18 may store the correlated data for time period $T_i$ for future reference, wherein the correlated data may include the raw orientation and/or EKG sensor data collected during $T_i$, the determined user orientation metric(s) for $T_i$, the determined EKG-based metric(s) for $T_i$, the current threshold values used for analyzing the data from $T_i$, and/or any other relevant information. Further, at 422, processing unit 18 may adjust one or more orientation threshold value(s) based on the correlated data stored at 420 for time period $T_i$ and/or correlated data stored at 420 for one or more prior time periods, and store such adjusted orientation threshold value(s). In some embodiments, processing unit 18 may adjust a magnitude component (e.g., X degrees), a duration component (e.g., Y minutes) of one or more particular orientation thresholds. Processing unit 18 may then use the adjusted orientation threshold value(s) at 408 for evaluating orientation data collected during subsequent time periods.

In this manner, processing unit 18 may learn user orientations that statistically correspond with abnormal EKG signals that trigger an aortocaval compression alert, regardless of whether such user orientation themselves trigger an orientation-based aortocaval compression alert (at 408). Processing unit 18 may then adjust one or more orientation threshold value(s) in order to subsequently trigger an orientation-based alert (based on the adjusted orientation threshold value(s)) before the abnormal EKG signals occur, to thereby preemptively prevent future aortocaval compression conditions. For example, assume processing unit 18 currently implements a right-side lateral tilt threshold of <40 degrees for a consecutive period of 10 minutes. Further assume that processing unit 18 triggers a number of EKG-signal alerts (due to EKG abnormalities) that correlate with a user orientation of <40 degree right-side lateral tilt for a consecutive period of between 8-10 minutes. Based on such learning, processing unit 18 may thus adjust the duration component of the right-side lateral tilt threshold to 7 minutes, such that processing unit 18 may subsequently trigger an orientation-based repositioning alert for an orientation of <40 degree right-side lateral tilt for a consecutive period of 7 minutes, which may thereby prompt a repositioning that preemptively avoids an abnormal EKG condition.

It should be understood that the parameters described with respect to algorithm 400, namely orientation metric(s) and maternal and/or fetal heart rate and/or heart rate variability, are examples only. Algorithm 400 or similar algorithm may be applied with respect to any other parameters, e.g., for learning-based adjustment of any suitable thresholds related to any parameter detected by system 10.

Figure 10:
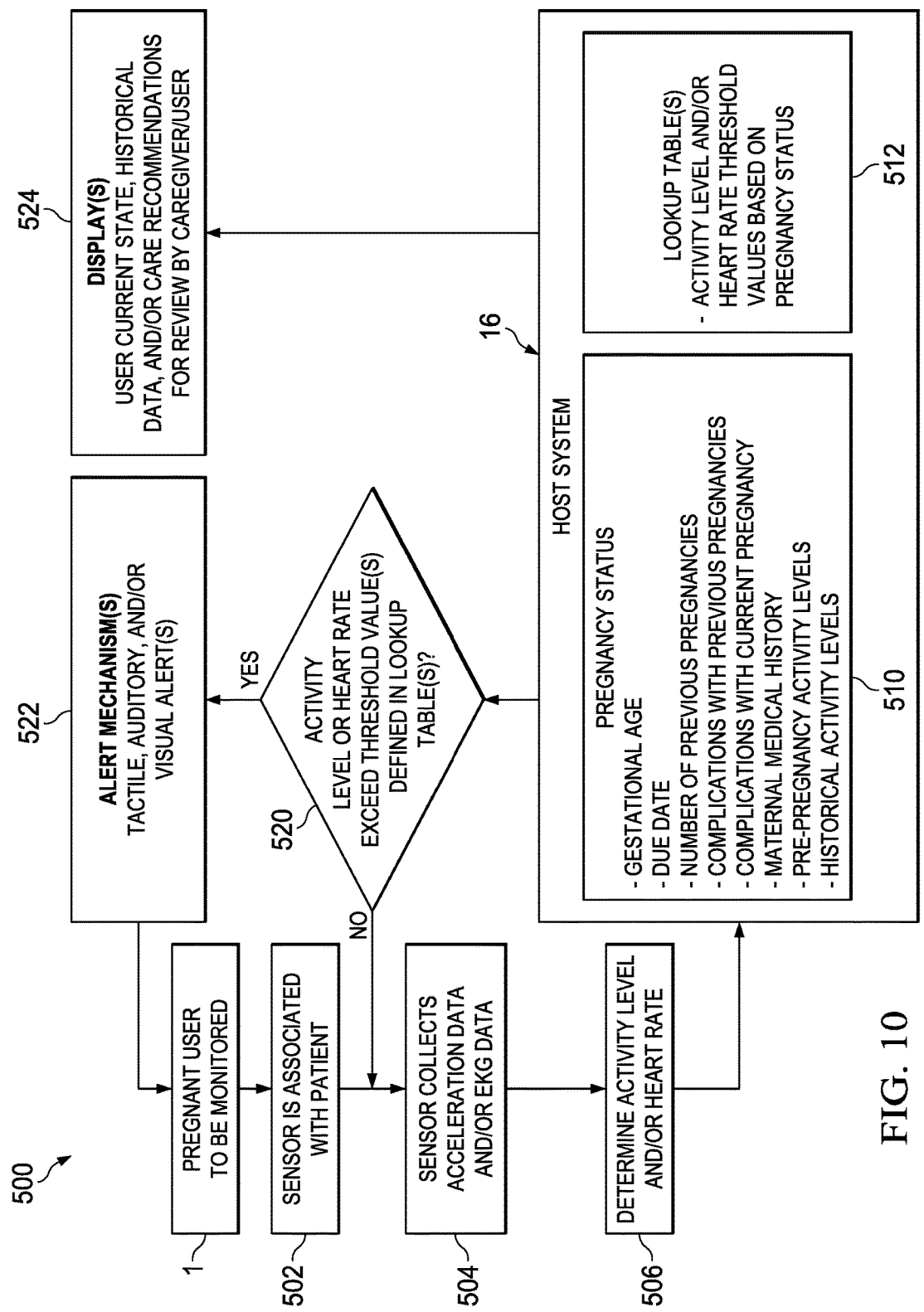
FIG. 10 illustrates an example algorithm for detecting and evaluating user activity level and/or heart rate as a function of pregnancy status, using relevant look-up tables, to detect an aortocaval compression condition, according to one embodiment.

FIG. 10 illustrates an example algorithm 500 for detecting and evaluating user activity level and/or heart rate as a function of pregnancy status, using relevant look-up tables, to detect an aortocaval compression condition, according to one embodiment. Algorithm 500 may be implemented by system 100, e.g., stored in storage unit 20 and executed by processing unit 18.

As shown, a user 1 (pregnant woman) to be monitored is identified, and a sensor device including sensor(s) 14, e.g., an accelerometer and/or EKG electrodes, may be secured directly or indirectly to the user at 502, e.g., on the abdomen proximate the umbilical. The sensor(s) 14 may include non-invasive EKG electrodes and/or other type(s) of sensors.

At 504, the sensor device collects sensor data, e.g., acceleration data and/or EKG data. At 506, processing unit 18 may determine one or more activity level metrics and/or heart rate metrics based on the sensor data collected at 504. With reference to items 510, 512, and decision step 520, processing unit 18 may then identify (or not) an aortocaval compression condition based on the activity level metric(s) and/or heart rate metric(s), as a function of pregnancy status 510, using one or more suitable lookup tables 512. The pregnancy status of the user may be defined by a set of pregnancy status parameters indicated at 510, which data may be stored in storage unit 20 (each pregnancy status parameters may be input via an input device 40 of system 10, or automatically determined by system 10, e.g., based on suitable sensor signals). As shown, the various pregnancy status parameter values may be displayed via a display device 524.

Lookup tables 512 may include (a) one or more tables defining activity level threshold values corresponding to different values of individual pregnancy status parameters or combinations of pregnancy status parameters defined at 510, and/or (b) one or more tables defining heart rate threshold values corresponding to different values of individual pregnancy status parameters or combinations of pregnancy status parameters defined at 510.

At 520, processing unit 18 may compare the activity level metric(s) and/or heart rate metric(s) with corresponding threshold value(s) determined from lookup table(s) 512, to determine the presence of an aortocaval compression condition. If no aortocaval compression condition is detected, the algorithm may return to 504 to collect and analyze further sensor data. However, if an aortocaval compression condition is detected, processing unit 18 may generate and output a repositioning alert to the user via an alert mechanism 30, as indicated at 522.

Positioning of Sensor Device on a User

The anatomy of a pregnant woman creates unique challenges for sensor placement, e.g., as it relates to monitoring for aortocaval compression, given the high degree of abdominal wall curvature. Thus, for a sensor placed on the surface of a pregnant woman's abdomen, slight changes in the right-to-left positioning of the sensor relative to the abdomen (e.g., relative to the umbilicus) may result in large changes in the degree of lateral tilt detected by the sensor, independent of any change in the orientation of the woman or her uterus. Similarly, slight changes in the longitudinal positioning (e.g., along the superior-inferior axis) of the sensor relative to the abdomen (e.g., relative to the umbilicus) may result in large changes in the degree of upright tilt detected by the sensor, independent of any change in the orientation of the woman or her uterus.

Because aortocaval compression generally occurs when a woman is lying predominantly flat/supine (i.e., zero or near-zero degrees of upright tilt) and with a low degree of lateral tilt (e.g., less than 15 degrees), the lateral tilt angle and/or upright tilt angle of the woman (as detected by an orientation sensor) may be used as input for identifying an aortocaval compression condition, as discussed herein. Thus, in some embodiments it is important to accurately determine the true lateral tilt angle and/or upright tilt angle of the woman.

Accordingly, in some embodiments it is important that the orientation sensor be secured in a known or determined location and orientation with respect to maternal anatomic landmarks. Thus, some embodiments provide a convenient and reliable way for a user to position a sensor with respect to anatomic landmarks (such as the umbilicus), such that the device can accurately determine the orientation of the uterus with respect to the aorta and inferior vena cava for use in identifying an aortocaval compression condition. In one embodiment, the sensor device may include indicia on the device housing, or the housing may have a shape that indicates an appropriate orientation, to provide a way for users to adhere the sensor to the body at a proper location and/or orientation. For example, in one embodiment, the sensor device has a donut shape intended for placement around the user's umbilicus, such that the umbilicus is positioned in the center of the donut.

FIG. 11 illustrates an example self-contained sensor device 10 having a housing 40 with a semicircular or crescent shape. Such sensor device 10 may be intended to be secured to the user such that the crescent shaped housing 40 partially surrounds the umbilicus in a laterally symmetrical manner as shown. Markings, patterns, or even the general shape of the sensor can be used to provide an indication as to which direction the sensor should be oriented, such as providing an arrow that is designed to point towards the user's head. A precise location and orientation of the sensor with respect to the user may thus be facilitated. In some embodiments the sensor device is designed to be secured proximate or relative to the umbilicus, or in the umbilical region, as this is a highly reliable anatomic landmark. In addition, lateral and upright tilt angles measured at this location may strongly correlate with the actual tilt angles of the uterus.

However, in other embodiments the sensor device is designed to be secured at other locations of the user's body, e.g., the upper torso, as long as the location can be defined or determined and that any orientation changes detected by the sensor reliably correlate with changes in the orientation of the uterus or other part of the body being monitored. Throughout this disclosure, references are made to the orientation, position, or angle of the uterus. Although not measured directly, the uterus is an intraabdominal organ that has a defined anatomic location relative to the surface of the abdomen. Therefore, by taking measurements from the surface of the abdomen and incorporating these known anatomic relationships, the orientation, position, or angle of the uterus can be determined. In particular, the relationship between the uterus and the great vessels, which run along the posterior abdominal wall, can be deduced.

In some embodiments, the sensor device is designed to be secured directly to the user, e.g., using an adhesive attachment mechanism. However, as discussed herein, any of a variety of attachment mechanisms may be provided for directly or indirectly securing the sensor device relative to the user. In some embodiments, proper attachment of the sensor to the user is actively monitored by system 10. In one embodiment, the sensor device includes a capacitive sensor to determine a measure of contact between the sensor device and the user's skin. If the measured capacitance falls outside of a threshold range, e.g., as a result of improper sensor attachment, system 10 may generate an alert to the user. Another method for monitoring sensor attachment involves detecting acceleration changes that are characteristic of proper attachment. For example, when a sensor is properly attached to a user, an accelerometer may detect rhythmic biomechanical activity, such as breathing and pulse. However, if the sensor device becomes detached from user, this rhythmic biomechanical activity may change dramatically in character or disappear completely, indicating the sensor device has become detached.

In one embodiment, the sensor device is adhesively attached to the user. However, given that the sensor may be intended for attachment to the user for a period of several days, weeks or months, the adhesive may not last for the entire duration of the monitoring period. Thus, in some embodiments, the adhesive and sensor device can be readily separated so that the adhesive can be replaced independently of the sensor module. In one embodiment, an adhesive layer can be applied to the user, and the sensor device housing can be attached to the adhesive layer in any suitable manner, e.g., magnetically. For example, the adhesive layer may include magnet(s) on an outer (non-adhesive) surface, and the sensor device may include magnet(s) on a back surface, such that when the sensor device and adhesive come into close proximity, they are magnetically attracted to each other and a magnetic attachment is provided. In embodiments in which capacitive sensing, bioimpedance sensing, EKG monitoring, or other skin surface sensing is used, the attachment apparatus may be designed to have electrical contact pass-throughs to enable such monitoring.

In some embodiments, the sensor device may contain two or more spatially separated accelerometers or other orientation sensors, such that system 10 can determine or estimate a curvature of the sensor device at the attachment location. System 10 may be configured to automatically determine or estimate the relative position of the sensor device with respect to the body based on the determined curvature of the sensor device. For example, if the sensor device extends circumferentially around the abdomen, and known anatomical relationships are provided to system 10 (e.g., the anterior portion of body is more curved than the posterior portion during pregnancy), then system 10 can automatically determine the relative location of the sensor device with respect to the body.

Further, system 10 may be configured to determine an abdominal circumference based on the detected curvature of the sensor device, and determine or estimate gestational age or fetal size/weight based on the abdominal circumference. Therefore, by measuring and tracking the abdominal circumference of a user, system 10 may be configured to provide an intrauterine growth chart or estimation of gestational age. Further, as the probability of aortocaval compression is related to the size of the uterus, system 10 can automatically set or adjust alert thresholds (used for identifying an aortocaval compression condition) based on the estimated size of the uterus.

The above example embodiments have been described hereinabove to illustrate various embodiments of implementing a system and method for targeting users based on demographic categorizations in a real-time online bidding system. Various modifications and departures from the disclosed example embodiments will occur to those having ordinary skill in the art. The subject matter that is intended to be within the scope of the present disclosure is set forth in the following claims.

The invention claimed is:

1. A monitoring system for monitoring for an aortocaval compression condition, the monitoring system comprising:
one or more sensors configured to be secured directly or indirectly to the user and configured to generate sensor signals;
a processor;
computer instructions stored in non-transitory computer-readable medium and executable by the processor to:
receive the sensor signals generated by the one or more sensors;
determine a physical orientation of the user based on the received sensor signals;
determine heart rate variability (HRV) data based on the received sensor signals, the heart rate variability data indicating at least one of (a) a heart rate variability of the user or (b) a heart rate variability of the fetus;
identify an aortocaval compression condition based at least on the determined physical orientation of the user and the determined HRV data; and
automatically generate and transmit an alert signal in response to identifying the aortocaval compression condition; and
an alert mechanism configured to receive the alert signal and output an alert to the user.

2. The monitoring system of claim 1, wherein the monitoring system comprises a self-contained device including the one or more sensors, the processor, and the non-transitory computer-readable medium storing the computer instructions.

3. The monitoring system of claim 1, wherein the HRV data determined based on the received sensor signals indicates a heart rate variability of the fetus.

4. The monitoring system of claim 1, wherein the HRV data determined based on the received sensor signals indicates a heart rate variability of the user.

5. The monitoring system of claim 1, wherein the computer instructions executable by the processor to determine HRV data based on the received sensor signals comprise computer instructions executable by the processor to determine HRV data based on a power spectra across a series of R-R intervals using a fast Fourier transformation.

6. The monitoring system of claim 1, wherein the computer instructions executable by the processor to determine HRV data based on the received sensor signals comprise computer instructions executable by the processor to determine HRV data using fractal dimensions.

7. The monitoring system of claim 1, wherein the computer instructions executable by the processor to determine HRV data based on the received sensor signals comprise computer instructions executable by the processor to determine HRV data using discrete wavelet transformations.

8. The monitoring system of claim 1, wherein the computer instructions executable by the processor to determine HRV data based on the received sensor signals comprise computer instructions executable by the processor to determine HRV data from an EKG signal.

9. The monitoring system of claim 1, wherein the computer instructions executable by the processor to identify the aortocaval compression condition based at least on the determined physical orientation of the user and the determined HRV data comprise computer instructions executable by the processor to:
determine a change in the HRV data corresponding with an indication of aortocaval compression; and
identify the aortocaval compression condition based on the determined change in the HRV data.

10. The monitoring system of claim 1, wherein the computer instructions executable by the processor to identify the aortocaval compression condition based at least on the determined physical orientation of the user and the determined HRV data comprise computer instructions executable by the processor to:
dynamically adjust an HRV threshold value over time;
compare the HRV data with the dynamically adjusted HRV threshold value over time; and
identify the aortocaval compression condition based on the comparison.

11. The monitoring system of claim 8, wherein the computer instructions executable by the processor to identify the aortocaval compression condition based at least on the determined physical orientation of the user and the determined HRV data comprise computer instructions executable by the processor to:
- determine an activity level of the user based on the received sensor signals;
- dynamically adjust an HRV threshold value over time based on the determined activity level of the user;
- compare the HRV data with the dynamically adjusted HRV threshold value over time; and
- identify the aortocaval compression condition based on the comparison.

* * * * *